(12) United States Patent
Haupt et al.

(10) Patent No.: US 8,586,557 B2
(45) Date of Patent: Nov. 19, 2013

(54) THERAPY OF P53 MUTANT COLON ADENOCARCINOMA, BREAST CANCER AND LUNG CANCER

(75) Inventors: Ygal Haupt, Hawthorn East (AU); Susan Haupt, Hawthorn East (AU)

(73) Assignee: Peter MacCallum Cancer Institute (AU)

( * ) Notice: Subject to any disclaimer, the term of this patent is extended or adjusted under 35 U.S.C. 154(b) by 128 days.

(21) Appl. No.: 12/731,374

(22) Filed: Mar. 25, 2010

(65) Prior Publication Data
US 2011/0081331 A1 Apr. 7, 2011

(30) Foreign Application Priority Data

Oct. 1, 2009 (AU) .............................. 2009222562

(51) Int. Cl.
*C12N 15/11* (2006.01)
*C12N 5/00* (2006.01)
*C07H 21/04* (2006.01)

(52) U.S. Cl.
USPC ..................... 514/44 A; 435/375; 536/24.5

(58) Field of Classification Search
None
See application file for complete search history.

(56) References Cited

U.S. PATENT DOCUMENTS 5,858,987 A * 1/1999 Beer-Romero et al. ...... 514/44 A
2009/0247607 A1* 10/2009 Benson et al. .............. 514/44 A

OTHER PUBLICATIONS

Rego et al., Role of promyelocytic leukemia (PML) protein in tumor suppression, 2001, The Journal of Experimental Medicine, vol. 193, pp. 521-529.*
Pier Paolo Pandolfi, Oncogenes and tumor suppressors in the molecular pathogenesis of acute promyelocytic leukemia, 2001, Human Molecular Genetics, vol. 10, pp. 769-775.*
Monte et al., MAGE-A tumor antigens target p53 transactivation function through histone deacetylase recruitment and confer resistance to chemotherapeutic agents, 2006, PNAS, vol. 103, pp. 11160-11165.*
Haupt et al., Promyelocytic leukemia protein is required for gain of function by mutant p53, Jun. 1, 2009, Cancer Research, vol. 69, pp. 4818-4826.*
Alsheich-Bartok et al., (2008) "PML enhances the regulation of p53 by CK1 in response to DNA damage," Oncogene, 27(26): 3653-61.
Blandino et al., (1999) "Mutant p53 gain of function: differential effects of different p53 mutants on resistance of cultured cells to chemotherapy," Oncogene, 18(2): 477-85.
Bischof et al., (2002) "Deconstructing PML-induced premature senescence," Embo J, 21(13): 3358-69.
Bode and Dong, (2004) Post-translational modification of p53 in tumorigenesis, Nat Rev Cancer, 4(10): 793-805.
Bolognese et al., (1999) "The cyclin B2 promoter depends on NF-Y, a trimer whose CCAAT-binding activity is cell-cycle regulated," Oncogene, 18(10): 1845-53.
Bossi et al., (2006) "Mutant p53 gain of function: reduction of tumor malignancy of human cancer cell lines through abrogation of mutant p53 expression," Oncogene, 25(2): 304-9.
Brummelkamp et al., (2002) "A system for stable expression of short interfering RNAs in mammalian cells," Science, 296(5567): 550-3.
Bruno et al., (2003) "The PML gene is not involved in the regulation of MHC class I expression in human cell lines," Blood, 101(9): 3514-9.
Bunz et al., (1999) "Disruption of p53 in human cancer cells alters the responses to therapeutic agents," J. Clin. Invest, 104: 263-269.
Cadwell and Zambetti, (2001) "The effects of wild-type p53 tumor suppressor activity and mutant p53 gain-of-function on cell growth," Gene, 277(1-2): 15-30.
Di Agostino et al., (2006) "Gain of function of mutant p53: the mutant p53/NF-Y protein complex reveals an aberrant transcriptional mechanism of cell cycle regulation," Cancer Cell, 10(3): 191-202.
Dittmer et al., (1993) "Gain of function mutations in p53," Nat Genet, 4(1): 42-6.
Everett et al., (2006) "PML contributes to a cellular mechanism of repression of herpes simplex virus type 1 infection that is inactivated by 'CPO," J Virol, 80(16): 7995-8005.
Fleckenstein et al., (2002) "Detection of p53 gene mutations by single strand conformational polymorphism (SSCP) in human acute myeloid leukemia-derived cell lines," Leuk Res, 26(2): 207-14.
Fogal et al., (2000) "Regulation of p53 activity in nuclear bodies by a specific PML isoform," Embo J, 19(22): 6185-95.
Guo et al., (2000) "The function of PML in p53-dependent apoptosis," Nat Cell Biol, 2(10): 730-6.
Gurrieri et al., (2004) "Loss of the tumor suppressor PML in human cancers of multiple histologic origins," J Natl Cancer Inst, 96(4): 269-79.
Imbriano et al., (2005) "Direct p53 transcriptional repression: in vivo analysis of CCAAT-containing G2/M promoters," Mol Cell Biol, 25(9): 3737-51.
Iwakuma and Lozano, (2007) "Crippling p53 activities via knock-in mutations in mouse models," Oncogene, 26(15): 2177-84.
Izquierdo et al., (2005) "Short interfering RNAs as a tool for cancer gene therapy," Cancer Gene Therapy, 12(3): 217-27.
Lang et al., (2004) "Gain of function of a p53 hot spot mutation in a mouse model of Li-Fraumeni syndrome," Cell, 119(6): 861-72.
Lavin and Gueven, (2006) "The complexity of p53 stabilization and activation," Cell Death Differ, 13(6): 941-50.

(Continued)

*Primary Examiner* — Dana Shin
(74) *Attorney, Agent, or Firm* — Banner & Witcoff, Ltd.

(57) ABSTRACT

The present invention provides a method for treating a hyperproliferative disorder characterized by expression of a mutant form of p53 in a subject, the method comprising administering to the subject a therapeutically effective amount of an agent which inhibits promyelocytic leukemia (PML) protein.

4 Claims, 18 Drawing Sheets
(14 of 18 Drawing Sheet(s) Filed in Color)

(56) References Cited

OTHER PUBLICATIONS

Li et al., (2008) "PTEN has tumor-promoting properties in the setting of gain-of-function p53 mutations," Cancer Res, 68(6): 1723-31.
Longo et al., (1993) "Frequency of RAS and p53 mutations in acute promyelocytic leukemias," Leuk Lymphoma, 11(5-6): 405-10.
Louria-Hayon et al., (2003) "The promyelocytic leukemia protein protects p53 from Mdm2-mediated inhibition and degradation," J Biol Chem, 278(35): 33134-41.
Manni et al., (2001) "NF-Y mediates the transcriptional inhibition of the cyclin BI, cyclin B2, and cdc25C promoters upon induced G2 arrest," J Biol Chem, 276(8): 5570-6.
Meulmeester and Jochemsen, (2008) "p53: a guide to apoptosis," Curr Cancer Drug Targets, 8(2): 87-97.
Mosmann, T., (1983) "Rapid colorimetric assay for cellular growth and survival: application to proliferation and cytotoxicity assays," J Immunol Methods, 65(1-2): 55-63.
Olive et al., (2004) "Mutant p53 gain of function in two mouse models of Li-Fraumeni syndrome," Cell, 119(6): 847-60.
Prives and White, (2008) "Does control of mutant p53 by Mdm2 complicate cancer therapy?" Genes & Dev, 22(10): 1259-64.
Quignon et al., (1998) "PML induces a novel caspase-independent death process," Nat Genet, 20(3): 259-65.
Saito et al., (2003) "Phosphorylation site interdependence of human p53 post-translational modifications in response to stress," J Biol Chem, 278(39): 37536-44.
Salomoni and Pandolfi, (2002) "The role of PML in tumor suppression," Cell, 108(2): 165-70.
Shaulsky et al., (1991) "Alterations in tumor development in vivo mediated by expression of wild type or mutant p53 proteins," Cancer Res, 51(19): 5232-7.
Sigal and Rotter, (2000) "Oncogenic mutations of the p53 tumor suppressor: the demons of the guardian of the genome," Cancer Res, 60(24): 6788-93.
St Clair et al., (2004) "DNA damage-induced downregulation of Cdc25C is mediated by p53 via two independent mechanisms: one involves direct binding to the cdc25C promoter," Mol Cell, 16(5): 725-36.
Strano et al., (2007) "Mutant p53 proteins: between loss and gain of function," Head Neck, 29(5): 488-96.
Strano et al., (2007) "Mutant p53: an oncogenic transcription factor," Oncogene, 26(15): 2212-9.
Summerton and Weller, (1997) "Antisense and Nucleic Acid Drug Development," 7: 187-195.
Tavalai et al., (2006) "Evidence for a role of the cellular ND 10 protein PML in mediating intrinsic immunity against human cytomegalovirus infections," J Virol, 80(16): 8006-18.
Terzian et al., (2008) "The inherent instability of mutant p53 is alleviated by Mdm2 or pl6INK4a loss," Genes & Dev, 22(10): 1337-44.
Trecca et al., (1994) "Analysis of p53 gene mutations in acute myeloid leukemia," Am J Hematol, 46(4): 304-9.
Trotman et al., (2006) "Identification of a tumour suppressor network opposing nuclear Akt function," Nature, 441(7092): 523-7.
Wang et al., (1998) "Role of PML in cell growth and the retinoic acid pathway," Science, 279(5356): 1547-51.
Xu et al., (2004) "Promyelocytic leukemia protein 4 induces apoptosis by inhibition of survivin expression," J Biol Chem, 279(3): 1838-44.
Zimber et al., (2004) "Nuclear bodies and compartments: functional roles and cellular signalling in health and disease," Cell Signal, 16(10): 1085-104.

Bowtell, "The genesis and evolution of high-grade serous ovarian cancer," Nat Rev Cancer. Nov. 2010;10(11): 803-8. Epub Oct. 14, 2010.
Bullock et al., "Rescuing the function of mutant p53," Nat Rev Cancer. Oct. 2001;1(1): 68-76.
Cao et al., "SUMOylation of HMGA2: selective destabilization of promyelocytic leukemia protein via proteasome," Mol Cancer Ther. Apr. 2008;7(4): 923-34.
Druker, "Perspectives on the development of a molecularly targeted agent," Cancer Cell. Feb. 2002;1(1): 31-6.
Haupt et al., "Mdm2 promotes the rapid degradation of p53," Nature. May 15, 1997;387(6630): 296-9.
Lallemand-Breitenbach et al., "Arsenic degrades PML or PML-RARalpha through a SUMO-triggered RNF4/ubiquitin-mediated pathway," Nat Cell Biol. May 2008;10(5): 547-55. Epub Apr. 13, 2008.
Louria-Hayon et al., "E6AP promotes the degradation of the PML tumor suppressor," Cell Death Differ. Aug. 2009;16 (8): 1156-66. Epub Mar. 27, 2009.
Pandolfi, "Oncogenes and tumor suppressors in the molecular pathogenesis of acute promyelocytic leukemia," Human Molecular Genetics. 2001; 10(7): 769-776.
Reineke et al., "Degradation of the tumor suppressor PML by Pin1 contributes to the cancer phenotype of breast cancer MDA-MB-231 cells," Mol Cell Biol. Feb. 2008;28(3): 997-1006. Epub Nov. 26, 2007.
Scaglioni et al., "A CK2-dependent mechanism for degradation of the PML tumor suppressor," Cell. Jul. 28, 2006;126 (2): 269-83.
Scian et al., "Modulation of gene expression by tumor-derived p53 mutants," Cancer Res. Oct. 15, 2004;64(20): 7447-54.
Tatham et al., "RNF4 is a poly-SUMO-specific E3 ubiquitin ligase required for arsenic-induced PML degradation," Nat Cell Biol. May 2008;10(5): 538-46. Epub Apr. 13, 2008.
Vassilev et al., "In vivo activation of the p53 pathway by small-molecule antagonists of MDM2," Science. Feb. 6, 2004;303(5659): 844-8. Epub Jan. 2, 2004.
Vickers et al., "The incidence of acute promyelocytic leukemia appears constant over most of a human lifespan, implying only one rate limiting mutation," Leukemia. Apr. 2000;14(4): 722-6 at p. 722, col. 1, ¶2.
Wang et al., "Small-molecule modulators of p53 family signaling and antitumor effects in p53-deficient human colon tumor xenografts," Proc Natl Acad Sci U S A. Jul. 18 2006;103(29): 11003-8. Epub 2006 Jul. 11, 2006.
Yang et al., "Pharmacological inhibition of BMK1 suppresses tumor growth through promyelocytic leukemia protein," Cancer Cell. Sep. 14, 2010;18(3): 258-67. Erratum in: Cancer Cell. Oct. 19, 2010;18(4): 396.
Berg, Randal W., et al.,"Tumor Growth Inhibition in Vivo and G2/M Cell Cycle Arrest Induced by Antisense Oligodeoxynucleotide Targeting Thymidylate Synthase," The Journal of Pharmacology and Experimental Therapeutics, Apr. 18, 2001, pp. 477-484, vol. 298, No. 2, The American Society for Pharmacology and Experimental Therapeutics.
Paruthiyil, Sreenivasan, et al.,"Estrogen Receptor β Inhibits Human Breast Cancer Cell Proliferation and Tumor Formation by Causing a G2 Cell Cycle Arrest" Cancer Research, Jan. 16, 2004, pp. 423-428, vol. 64, American Association for Cancer Research.
Ventura, Andrea, et al.,"Restoration of p53 Function Leads to Tumor Regression in Vivo," Nature, Feb. 8, 2007, pp. 661-665, vol. 445, Nature Publishing Group.

\* cited by examiner

FIGURE 3A-D
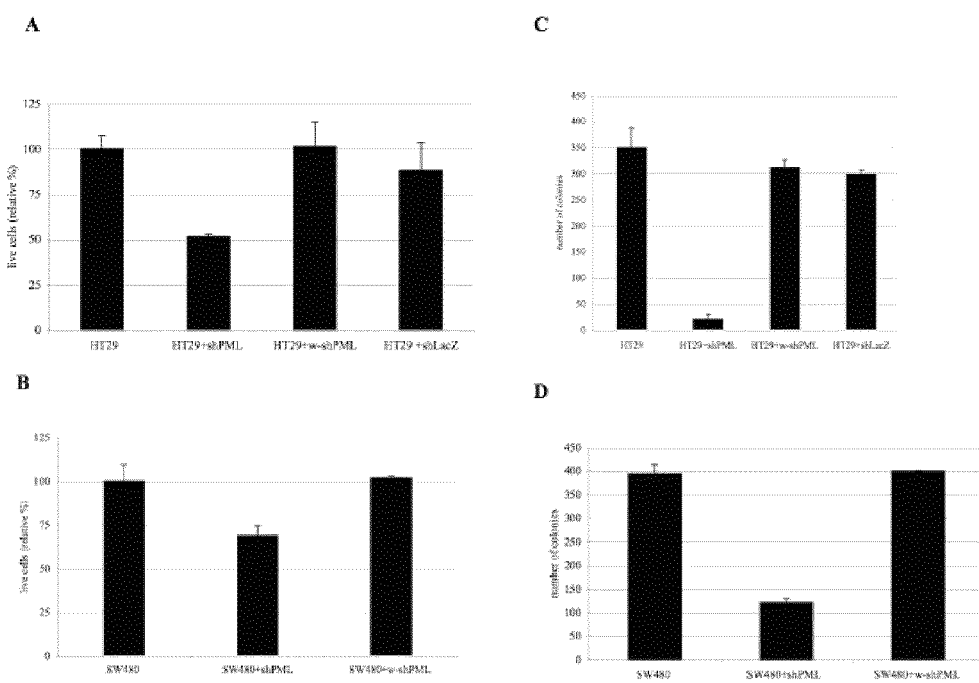

FIGURE 3E-F
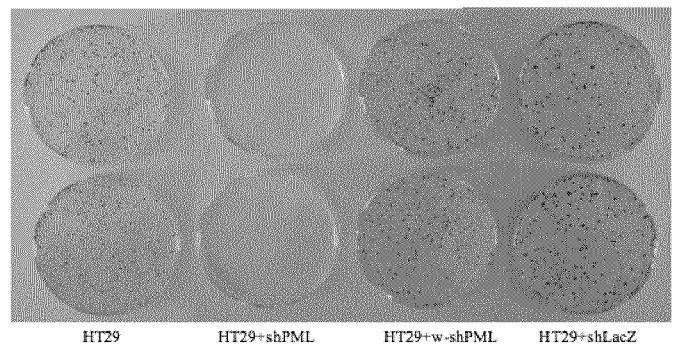
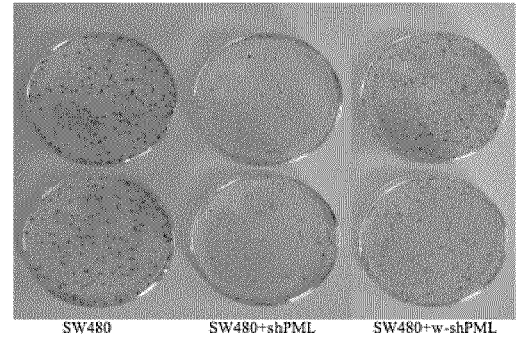

FIGURE 4B-C
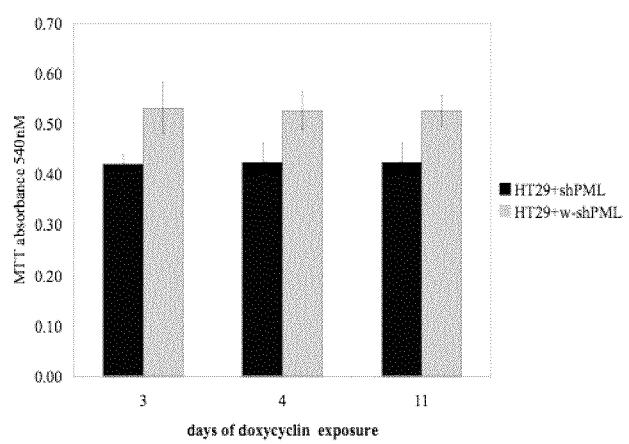
Haupt Figure 4B
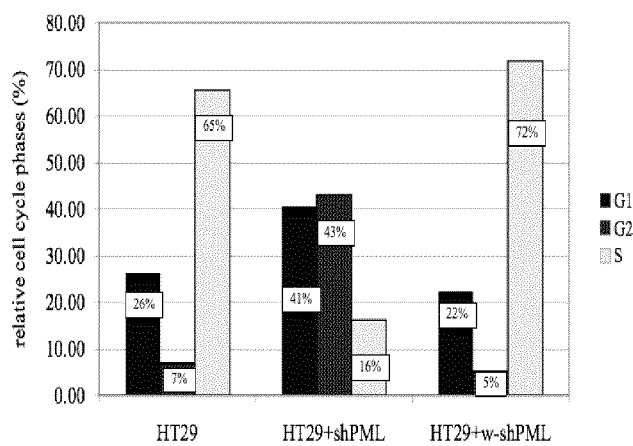

FIGURE 5A-B
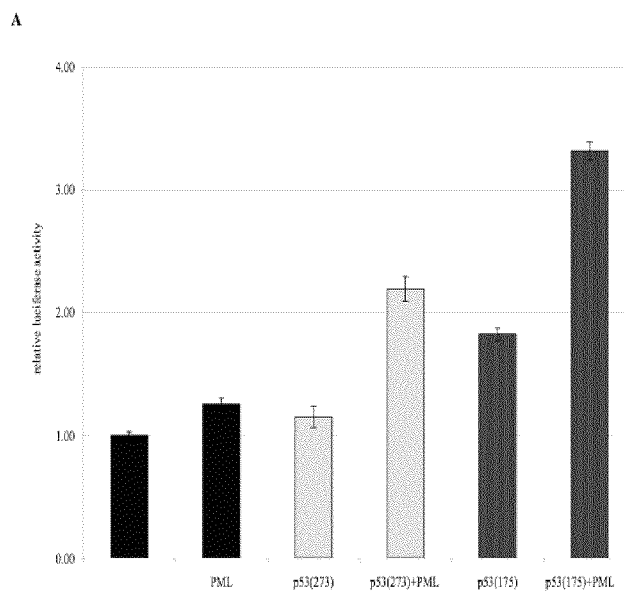
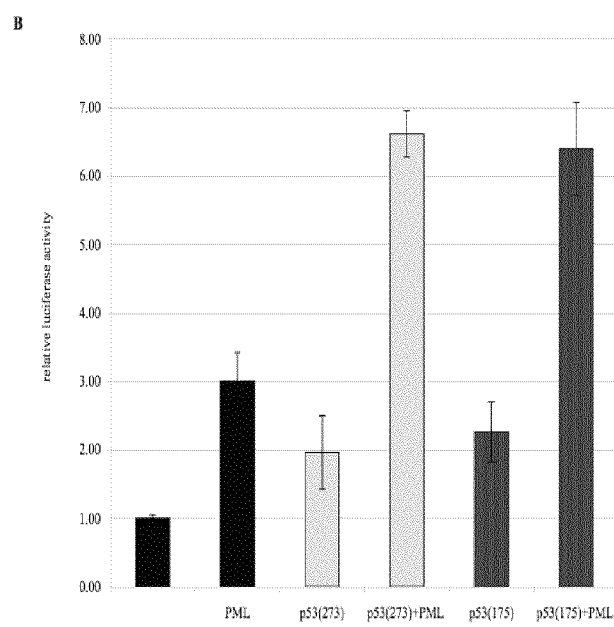

Bi ii

Haupt Supplemental Figure 1

THERAPY OF P53 MUTANT COLON ADENOCARCINOMA, BREAST CANCER AND LUNG CANCER

FIELD OF THE INVENTION

The present invention relates generally to methods for cancer therapy. More particularly, the present invention provides methods for the treatment of cancer and other hyperproliferative disorders by modulating the expression and/or activity of promyelocytic leukemia (PML) protein.

This application incorporates by reference the contents of a 3 kb text file created on Mar. 23, 2010 and named "004244_00006_Seqlisting.txt," which is the sequence listing for this application.

BACKGROUND

Bibliographic details of the publications referred to by number in this specification are collected at the end of the description.

The development of small therapeutic agents is a major goal in the pharmaceutical industry. Such agents are potentially relatively inexpensive to manufacture and are less likely to induce adverse immunological responses. One of the difficulties, however, in small therapeutic molecule development is target selection. Many potential targets lack suitability due to their pleiotropic nature and/or due to the level of redundancy in a particular pathway.

p53 (also known as protein 53 or tumour protein 53), is a transcription factor which in humans is encoded by the TP53 gene. p53 is important in multicellular organisms, where it regulates the cell cycle and functions as a tumor suppressor that is involved in the prevention of cancer. As such, p53 has been described as "the guardian of the genome," "the guardian angel gene," and the "master watchman", referring to its role in conserving stability by preventing genome mutation.

p53 mutation can corrupt the tumor suppressive functions of the wild type (wt) protein. In response to specific cellular stresses, wt p53 either initiates a temporary interruption of the cell cycle to enable DNA repair or triggers cellular senescence or apoptosis when damage is excessive (reviewed in Meulmeester et al.). In contrast, cells bearing common p53 mutations are released from these constraints. Further, certain p53 mutations may acquire distinct properties from the wild type counterpart, referred to as a "gain of function" (GOF) phenomena (reviewed in Strano et al. (*Head Neck*)). The contribution of certain p53 mutations to chemotherapeutic drug resistance was demonstrated in human cancer cells cultured in vitro (reviewed in Sigal et al. and Strano et al. (*Oncogene*)). A role for mutant p53 in the development and spread of the tumors was also corroborated by these studies. The most compelling evidence for the GOF of mutant p53 was demonstrated in knock-in (KI) mutant p53 mice, which developed tumors with a distinct spectrum from p53+/− or −/− mice. Furthermore, tumors in these KI mice exhibited an enhanced metastatic potential (Lang et al. and Olive et al.)

Wild-type p53 is subject to tight regulation that is affected through protein-protein interactions and by extensive post-translational modifications (Lavin et al. and Bode et al.). In contrast, less is known about the regulation of mutant p53, although mutant p53 is subject to at least certain modifications (Bode et al.). Strikingly, higher mutant p53 levels have been identified in (most) tumor cells than in the surrounding healthy tissues of mutant p53 KI mice (Iwakuma et al.). Recent work by Terzian et al. demonstrated that, as in the case of wt p53, the stabilization of mutant p53 is regulated by Mdm2. Mice lacking mdm2 express higher levels of mutant p53 succumb earlier and develop metastatic tumours (Terzian et al. and Prives et al.).

Certain modifications of wt p53 are regulated by the promyelocytic leukemia (PML) protein (Zimber et al.). PML is a key factor in the formation of PML nuclear bodies, which are distinct nuclear multi-protein complexes that have been associated with critical cellular processes, including tumor suppression, gene regulation, post-translational modifications and protein catabolism (reviewed in Zimber et al. and Salomoni et al.). PML knock-out mice develop normally, but are resistant to lethal doses of γ-irradiation (IR; Guo et al.). In addition, they are prone to tumorigenesis in response to carcinogens (Wang et al.), or an additional oncogenic event, such as the loss of PTEN (Trotman et al.). In humans, a complete or partial loss of PML has been observed in multiple types of cancers, including breast colon and prostate (Gurrieri et al.). PML is therefore considered as a bona-fide tumour suppressor.

WO 2009/063426 discloses siRNA mediated knock-down of the PML/RARα (retonoic acid receptor alpha) complex which inhibits the growth of Acute Promyelocytic Leukemia (APL) cells. However, it is the chromosomal translocation t(15; 17) of the PML gene which causes the formation of an aberrant fusion protein between PML and RARα. RARα then targets the complex to myeloid specific genes with consequent inhibition of myeloid cell differentiation. Thus, the siRNA is used to target a mutant form of PML specifically for the treatment of Acute Myeloid Leukemia (AML).

US 2003/0207791 discloses methods for the treatment of a disease associated with the formation of high molecular weight complexes of chimeric transcription factors. This includes PML/RARα and its use in the treatment of acute myeloid leukemias. Again, the agent is used to target a specific transcription factor complex for the treatment of AML.

The regulation of mutant p53 and the cellular events leading to tumour cell growth and associated hyperproliferative disease is not well understood. Identifying possible cellular targets which affect the growth and/or survival of tumour cells characterized by mutant p53 expression may lead to the identification and development of effective cancer therapies.

SUMMARY OF THE INVENTION

In a first aspect of the present invention there is provided a method for treating a hyperproliferative disorder characterized by expression of a mutant form of p53 in a subject, the method comprising administering to the subject a therapeutically effective amount of an agent which inhibits promyelocytic leukemia (PML) protein.

In a second aspect of the present invention there is provided a method for inhibiting the survival and/or proliferation of tumour cells expressing a mutant form of p53, the method comprising exposing the tumour cells to an effective amount of an agent which inhibits promyelocytic leukemia (PML) protein.

In a third aspect of the present invention there is provided a pharmaceutical composition comprising a therapeutically effective amount of an agent which inhibits promyelocytic leukemia (PML) protein for treating a hyperproliferative disorder in a subject in need thereof.

In a fourth aspect of the present invention there is provided an agent which inhibits promyelocytic leukemia (PML) protein for treating a hyperproliferative disorder in a subject in need thereof.

In a fifth aspect of the present invention there is provided a use of a therapeutically effective amount of an agent which inhibits promyelocytic leukemia (PML) protein for the manufacture of a medicament for treating a hyperproliferative disorder in a subject in need thereof.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

Figure 1A:
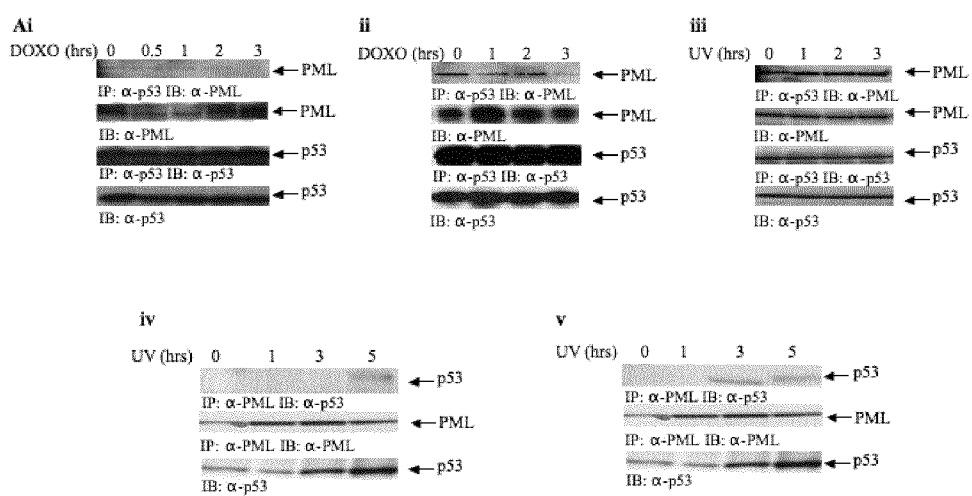
FIG. 1 shows mutant p53 and PML interact without extracellular stress. (A) cells bearing either mutant ((i) HT29; (ii) SW480; and (iii) SKBR3) or wt p53 ((iv) HCT116 p53+/+; and (v) MCF7) were subjected to UV (40 μJ×100) or doxorubicin (2 μg/mL, 1 h) as indicated, harvested at designated times, and subjected to immunoprecipitation and blotting with either a consecutive combination of polyclonal antibodies to p53 (FL393 goat) then PML (Sigma Chemicals; (i-iii)), or PML (Sigma Chemicals) then polyclonal antibodies to p53 (FL393 rabbit; (iv and v)). (B) SW480 cells were plated on coverslips and 24 h later were fixed and subjected to immunofluorescent staining. p53 was stained with the simultaneous exposure of DO1 and 1801 antibodies in conjunction with goat anti-mouse FITC-conjugated secondary antibody (green). PML was detected using anti-PML polyclonal antibody rhodamine conjugate (red, PG-M3 TRITC). Cells were visualized using an Olympus FV1000 confocal microscope (×60 objective, zoom 2.5). Right, merged images (yellow, colocalization). (C) MCF7 cells bearing wt p53 were plated on coverslips and 24 h subsequently were alternatively either left untreated or exposed to doxorubicin (2 μg/mL for 1 h), washed out and harvested after an additional 6 h. Fixed cells were either DNA-stained with DAPI or with anti-PML polyclonal antibodies in conjunction with Cy5-conjugated secondary antibody (red) and p53 monoclonal antibodies followed by Cy2-conjugated secondary antibody (green).

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

It is to be understood that unless otherwise indicated, the subject invention is not limited to specific manufacturing methods, formulation components, dosage regimens, or the like, as such may vary. It is also to be understood that the terminology used herein is for the purpose of describing particular embodiments only and is not intended to be limiting.

It must be noted that, as used in the subject specification, the singular forms "a", "an" and "the" include plural aspects unless the context clearly dictates otherwise. Thus, for example, reference to "an agent" includes a single agent, as well as two or more agents; reference to "the composition" includes a single composition, as well as two or more compositions; and so forth.

The present invention is predicated on the surprising discovery that promyelocytic leukemia (PML) protein is shown to be an important regulator of mutant p53 by enhancing the transcriptional activity of mutant p53. Unexpectedly, the present inventors demonstrate that PML is required for the proliferation and colony formation of cancer cells bearing mutant p53, and is important for its "gain of function" phenotype in cultured human cancer cells.

Accordingly, in one embodiment of the present invention there is provided a method for treating a hyperproliferative disorder characterized by expression of a mutant form of p53 in a subject, the method comprising administering to the subject a therapeutically effective amount of an agent which inhibits promyelocytic leukemia (PML) protein.

Each embodiment described in this specification is to be applied *mutatis mutandis* to every other embodiment unless expressly stated otherwise.

The term "hyperproliferative disorder" as used herein is intended to include any disease state, disorder or condition which results from the uncontrolled proliferation of any cell type(s) in which expression of mutant p53 is involved. This includes cancer, which examples may include, but are not limited to, ovarian, colorectal, esophagus, head and neck, larynx, skin, pancreas, stomach, liver, brain, bladder, uterus, prostate, bones, endocrine glands, leukemias, lymphomas and other hematological malignancies, soft tissues, lung, breast, cervix and colon cancers.

The term "agent which inhibits promyelocytic leukemia (PML) protein" as used herein is intended to include any agent which inhibits, suppresses, decreases, antagonizes, modulates and/or down-regulates the level of expression of a gene encoding PML protein, inhibits, suppresses, decreases, antagonizes, modulates and/or down-regulates the expression of PML protein, or inhibits, suppresses, decreases, antagonizes and/or modulates the accumulation or activity of PML protein.

The term "gene" is used in its broadest sense and includes cDNA corresponding to the exons of a gene. Reference herein to a "gene" is also taken to include: a classical genomic gene consisting of transcriptional and/or translational regulatory sequences and/or a coding region and/or non-translated sequences (i.e. introns, 5'- and 3'-untranslated sequences); or mRNA or cDNA corresponding to the coding regions (i.e. exons) as well as 5'- and 3'-untranslated sequences of the gene.

The term "subject" as used herein refers to an animal, in particular a mammal and more particularly a primate including a lower primate and even more particularly, a human who can benefit from the medical protocol of the present invention. A subject regardless of whether a human or non-human animal or embryo may be referred to as an individual, subject, animal, patient, host or recipient. The present invention has both human and veterinary applications. For convenience, an "animal" specifically includes livestock animals such as cattle, horses, sheep, pigs, camelids, goats and donkeys. With respect to horses, these include horses used in the racing industry as well as those used recreationally or in the livestock industry. Examples of laboratory test animals include mice, rats, rabbits, guinea pigs and hamsters. Rabbits and rodent animals, such as rats and mice, provide a convenient test system or animal model as do primates and lower primates.

In another embodiment of the present invention there is provided method for inhibiting the survival and/or proliferation of tumour cells expressing a mutant form of p53, the method comprising exposing the tumour cells to an effective amount of an agent which inhibits promyelocytic leukemia (PML) protein.

The term "agent which inhibits promyelocytic leukemia (PML) protein" has been defined above. In the context of inhibiting the survival and/or proliferation of tumour cells expressing a mutant form of p53 therefore includes any agent which inhibits, suppresses, decreases, antagonizes and/or modulates the survival and/or proliferation of tumour cells expressing a mutant form of p53.

Examples of agents according to the present invention include, but are not limited to, RNA including sense RNAs, antisense RNAs, mRNAs, tRNAs, rRNAs, small interfering RNAs (SiRNAs), double-stranded RNAs (dsRNA), short hairpin RNAs (shRNAs), piwi-interacting RNAs (PiRNA), micro RNAs (miRNAs), small nucleolar RNAs (SnoRNAs), small nuclear (SnRNAs), ribozymes, aptamers, DNAzymes or other ribonuclease-type complexes. Methods of producing chimeric constructs capable of inducing RNA interference in eukaryotic cells are described in the art.

RNA interference (RNAi) is used generally to refer to the endogenous process of gene silencing involving double stranded (sense and antisense) RNA which leads to sequence specific reduction in gene expression via target mRNA degradation. RNAi is typically mediated by short double stranded siRNAs, short or small hairpin RNAs, or single stranded microRNAs (miRNA). Broadly, RNAi is initiated when a strand of RNA from either of these molecules forms a complex referred to as an RNA-induced silencing complex (RISC) which targets complementary RNA and suppresses translation. The process has been exploited for research purposes and for therapeutic application (see for example Izquierdo et al). Other oligonucleotides having RNA-like properties have also been described and many more different types of RNAi may be developed. Antisense and iRNA compounds may be double stranded or single stranded oligonucleotides which are RNA or RNA-like or DNA or DNA-like molecules that hybridize specifically to DNA or RNA of PML encoding sequences. iRNA compounds are typically approximately 8 to 80 nucleobases in length and specifically hybridize to a nucleic acid region encoding PML protein as further described herein or as known in the art.

siRNA may have a first strand and a second strand each strand being approximately 20 to 25 nucleobases in length with the strands being complementary over at least about 19 nucleobases and having on each 3' termini of each strand a deoxy thymidine dimer (dTdT) which in the double-stranded compound acts as a 3' overhang. Alternatively, the double-stranded antisense compounds are blunt-ended siRNAs. Alternatively, single-stranded RNAi (ssRNAi) compounds that act via the RNAi antisense mechanism are contemplated. Further modifications can be made to the double-stranded compounds and may include conjugate groups attached to one of the termini, selected nucleobase positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double-stranded. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

A small hairpin RNA or short hairpin RNA (shRNA) is a sequence of RNA that makes a tight hairpin turn that can be used to silence gene expression via RNA interference. shRNA uses a vector introduced into cells and utilizes the U6 promoter to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs which match the siRNA that is bound to it.

In certain embodiments of the present invention the agent is selected from the group consisting of shRNA, siRNA, miRNA, DNAzyme, ribozyme, antisense and morpholino or other iRNA molecule targeted against PML mRNA, and preferably a shRNA or siRNA targeted against PML mRNA.

In other embodiments of the present invention the agent is a shRNA targeted against PML mRNA and consists in a sequence selected from the group consisting of:

```
GACCAACAACATCTTCTGC        (SEQ ID No: 1)
and
```
```
AGATGCAGCTGTATCCAAG.       (SEQ ID No: 2)
```

In yet other embodiments of the present invention the agent is a siRNA targeted against the PML mRNA sequence which mRNA consists in a sequence GAGTCGGCCGACTTCTGGT (SEQ ID No: 3).

Antisense polynucleotide sequences are also examples of suitable agents according to the present invention. Polynucleotide vectors, for example, containing all or a portion of PML gene sequences or gene flanking sequences may be placed under the control of a promoter in an antisense orientation and introduced into a cell. Expression of such an antisense construct within a cell will interfere with gene transcription and translation. Furthermore, co-suppression and mechanisms to induce RNAi (i.e. siRNA or miRNA) may also be employed. Alternatively, antisense or sense molecules may be directly administered. In this latter embodiment, the antisense or sense molecules may be formulated in a composition and then administered by any number of means to target cells.

A variation on antisense and sense molecules involves the use of morpholinos, which are oligonucleotides composed of morpholine nucleotide derivatives and phosphorodiamidate linkages (for example Summerton and Weller). Morpholino nucleic acids typically comprise heterocyclic bases attached to the morpholino ring. A number of linking groups may link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based oligomeric compounds are non-ionic mimics of oligonucleotides which are less likely to form undesired interactions with cellular proteins. Morpholino-based oligomeric compounds are disclosed in U.S. Pat. No. 5,034,506; WO 00024885 and WO 00045167.

While oligonucleotides is one embodiment of agent for this invention, the present invention comprehends other families of compounds as well, including but not limited to oligonucleotide analogs, chimeric, hybrid and mimetic forms.

The compounds in accordance with this invention preferably comprise from about 8 to about 80 nucleobases (i.e. from about 8 to about 80 linked nucleosides). One of ordinary skill in the art will appreciate that the invention embodies compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones containing a phosphorus atom therein include, for example, phosphorothioates, chiral phosphoro-thioates, phosphoro-dithioates, phosphotri-esters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included. Many of the preferred features described above are appropriate for sense nucleic acid molecules.

In certain embodiments, the method is achieved by cleavage of PML mRNA by a sequence-specific DNAzyme. In a further embodiment, the DNAzyme comprises (i) a catalytic domain which cleaves mRNA at a purine:pyrimidine cleavage site; (ii) a first binding domain contiguous with the 5' end of the catalytic domain; and (iii) a second binding domain contiguous with the 3' end of the catalytic domain, wherein the binding domains are sufficiently complementary to two regions immediately flanking a purine: pyrimidine cleavage site within the PML mRNA such that the DNAzyme cleaves the c-Jun mRNA.

The term "DNAzyme" as used herein means a DNA molecule that specifically recognizes and cleaves a distinct target nucleic acid sequence, which may be either DNA or RNA. In certain embodiments, the binding domains of the DNAzyme are complementary to the regions immediately flanking the cleavage site. It will be appreciated by those skilled in the art, however, that strict complementarity may not be required for the DNAzyme to bind to and cleave the PML mRNA.

The binding domain lengths (also referred to herein as "arm lengths") can be of any permutation, and can be the same or different. In certain embodiments, the binding domain lengths are at least 6 nucleotides. Preferably, both binding domains have a combined total length of at least 14 nucleotides. Various permutations in the length of the two binding domains, such as 7+7, 8+8 and 9+9, are envisioned.

In applying DNAzyme-based treatments, it is preferable that the DNAzymes be as stable as possible against degradation in the intra-cellular milieu. One means of accomplishing this is by incorporating a 3'-3' inversion at one or more termini of the DNAzyme. More specifically, a 3'-3' inversion (also referred to herein simply as an "inversion") means the covalent phosphate bonding between the 3' carbons of the terminal nucleotide and its adjacent nucleotide. This type of bonding is opposed to the normal phosphate bonding between the 3' and 5' carbons of adjacent nucleotides, hence the term "inversion".

Accordingly, in certain embodiments of the present invention, the 3'-end nucleotide residue is inverted in the building domain contiguous with the 3' end of the catalytic domain. In addition to inversions, the instant DNAzymes may contain modified nucleotides. Modified nucleotides include, for example, N3'-P5' phosphoramidate linkages, and peptide-nucleic acid linkages. These are well known in the art. In a particularly preferred embodiment, the DNAzyme includes an inverted T at the 3' position.

In another embodiment, the agent is a sequence-specific hammerhead ribozyme and derivative of the hammerhead ribozyme such as the Minizymes or Mini-ribozymes or where the ribozyme is derived from: (i) the hairpin ribozyme, (ii) the Tetrahymena Group I intron, (iii) the Hepatitis Delta Viroid ribozyme or (iv) the Neurospera ribozyme.

It will be appreciated by those skilled in the art that the composition of the ribozyme may be; (i) made entirely of RNA, (ii) made of RNA and DNA bases, or (iii) made of RNA or DNA and modified bases, sugars and backbones Within the context of the present invention, the ribozyme may also be either; (i) entirely synthetic or (ii) contained within a transcript from a gene delivered within a virus-derived vector, expression plasmid, a synthetic gene, homologously or heterologously integrated into the patients genome or delivered into cells ex vivo, prior to reintroduction of the cells of the patient, using one of the above methods.

An additional example of an agent according to the present invention is E3 ligase E6AP. The catalytically active form of the mammalian E3 ligase E6AP (HPV E6 Associated Protein) acts to reduce the half life of the PML protein by promoting its degradation in the ubiquitin proteosome system. E6AP mediates the ubiquitination of PML in vivo and in vitro. Accordingly, in certain embodiments of the present invention, the agent is E3 ligase E6AP. Preferably, the E3 ligase E6AP is activated or over-expressed. Activation of E6AP implies that its enzymatic or catalytic E3 ligase activity is increased beyond the base line (or basal) level. Over-expressed E6AP implies that the expression level of E6AP is higher than the base (or basal) line level. This could be due to amplification of the E6AP gene, or enhanced transcription or translation of its mRNA.

By targeting PML, the methods and compositions of the present invention inhibit the accumulation of promyelocytic leukemia nuclear bodies (PML-NBs). PML-NBs are distinct nuclear multi-protein complexes that have been implicated in the regulation of growth inhibition, senescence and apoptosis.

Reference to "PML" as used herein includes isoforms, mutants, variants, and homologs or orthologs from other species, including, without limitation, murine and human forms. In certain embodiments of the present invention, the agents are derived from nucleic acid molecules such as the nucleotide sequences of PML as described herein (isoform I: NM_033238; isoform II: NM_033239; isoform IV: NM-002675; isoform V: NM_033240) or variants thereof. Variants include nucleic acid molecules sufficiently similar to naturally occurring forms of these molecules or their complementary forms over all or part thereof such that selective hybridisation may be achieved under conditions of medium or high stringency, or which have about 60% to 90% or 90 to 98% sequence identity to the nucleotide sequences defining naturally occurring PML DNA or RNA sequences as described herein and over a comparison window comprising at least about 15 nucleotides. Preferably the hybridisation region is about 12 to about 18 nucleobases or greater in length. Preferably, the percent identity between a particular nucleotide sequence and the reference sequence is at least about 80%, or 85%, or more preferably about 90% similar or greater, such as about 95%, 96%, 97%, 98%, 99% or greater. Percent identities between 80% and 100% are encompassed. The length of the nucleotide sequence is dependent upon its proposed function. For example, short interfering RNAs are generally about 20 to 24 nucleotides in length, whereas molecules designed to provide dominant negative functions may require full length or substantially full length molecules.

The term "homolog" or "homologs" refers broadly to functionally and structurally related molecules including those from other species. Isoforms, mutants, homologs and orthologs are examples of variants.

In some embodiments the present invention contemplates the use of full length PML polypeptide or biologically active components or portions (fragments) or stapled peptides of one or more of these molecules as antagonists. Biologically active portions or peptides comprise one or more binding domains. A biologically active portion or stapled peptide of a full length polypeptide can be a polypeptide which is, for example, 4, 5, 6, 7, 8, 9, 10, 11, 12, 13, 14, 15, 16, 17, 18, 19, 20, 21, 22, 23, 24, 25, 30, 40, 50, 60, 70, 80, 90, 100, 120, 150, 300, 350, or 400 or more amino acid residues in length. The PML polypeptide contemplated herein include all biologically active or naturally occurring forms of as well as biologically active portions and variants thereof.

"Variant" polypeptides include proteins derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is, they continue to possess at least one biological activity of the native protein. Antagonist variants are selected on the basis that they inhibit or antagonise the biological activity or formation of PML or its encoding genes. Such variants may result from, for example, genetic polymorphism or from human manipulation. Biologically active variants of a native PML polypeptide will have at least 40%, 50%, 60%, 70%, generally at least 75%, 80%, 85%, preferably about 90% to 95% or more, and more preferably about 98% or more sequence similarity with the amino acid sequence for the native protein as determined by contemporary sequence alignment programs using default parameters. A biologically active variant of a PML polypeptide may differ from that polypeptide generally by as much 100, 50 or 20 amino acid residues or suitably by as few as 1-15 amino acid residues, as few as 1-10, such as 6-10, as few as 5, as few as 4, 3, 2, or even 1 amino acid residue.

Variant polypeptides or peptides may contain conservative amino acid substitutions at various locations along their sequence, as compared to reference amino acid sequences. A "conservative amino acid substitution" is one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

The agents according to the present invention are to be administered in an effective amount. The terms "effective amount" and "therapeutically effective amount" of an agent as used herein mean a sufficient amount of the agent to provide in the course the desired therapeutic or physiological effect in at least a statistically significant number of subjects. Undesirable effects, e.g. side effects, are sometimes manifested along with the desired therapeutic effect; hence, a practitioner balances the potential benefits against the potential risks in determining what is an appropriate "effective amount". The exact amount required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using only routine experimentation. In some embodiments, an effective amount for a human subject lies in the range of about 0.1 ng/kg body weight/dose to 1 g/kg body weight/dose. In some embodiments, the range is about 1μ to 1 g, about 1 mg to 1 g, 1 mg to 500 mg, 1 mg to 250 mg, 1 mg to 50 mg, or 1μ to 1 mg/kg body weight/dose. Dosage regimes are adjusted to suit the exigencies of the situation and may be adjusted to produce the optimum therapeutic dose. For example, several doses may be provided daily, weekly, monthly or other appropriate time intervals.

Hence, in certain embodiments of the present invention there is provided a pharmaceutical composition comprising a therapeutically effective amount of an agent which inhibits promyelocytic leukemia (PML) protein for treating a hyperproliferative disorder in a subject in need thereof. The present invention also contemplates a pharmaceutical composition comprising a therapeutically effective amount of an agent which inhibits promyelocytic leukemia (PML) protein for inhibiting the survival and/or proliferation of tumour cells expressing a mutant form of p53.

The term "agent which inhibits the induction of a gene encoding promyelocytic leukemia (PML) protein" has been defined above.

In certain embodiments of the present invention the hyperproliferative disorder is cancer. The term cancer is intended to cover any cancer characterized by expression of mutant p53, which includes, but is not limited to, ovarian, colorectal, esophagus, head and neck, larynx, skin, pancreas, stomach, liver, brain, bladder, uterus, prostate, bones, endocrine glands, leukemias, lymphomas and other hematological malignancies, soft tissues, lung, breast, cervix and colon cancers.

The active agent according to the invention may be administered in a single dose or a series of doses. While it is possible for the active ingredient to be administered alone, it is preferable to present it as a composition, preferably as a pharmaceutically composition. The formulation of such compositions is well known to those skilled in the art. The composition may contain any pharmaceutically acceptable carriers, diluents or excipients.

Suitable dosage amounts and dosing regimens can be determined by the attending physician and may depend on the particular condition being treated, the severity of the condition as well as the general age, health and weight of the subject.

By "pharmaceutically acceptable" carrier, excipient or diluent is meant a pharmaceutical vehicle comprised of a material that is not biologically or otherwise undesirable, i.e. the material may be administered to a subject along with the selected active agent without causing any or a substantial adverse reaction. Carriers may include excipients and other additives such as diluents, detergents, coloring agents, wetting or emulsifying agents, pH buffering agents, preservatives, and the like. Carriers may also include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

Similarly, a "pharmacologically acceptable" salt, ester, amide, prodrug or derivative of a compound as provided herein is a salt, ester, amide, prodrug or derivative that this not biologically or otherwise undesirable.

Delivery of the nucleic acids described may also be achieved via one or more, of the following non-limiting examples of vehicles: (a) liposomes and liposome-protein conjugates and mixtures; (b) non-liposomal lipid and cationic lipid formulations; (c) activated dendrimer formulations; (d) within a polymer formulation such as polyethylenimine (PEI) or pluronic gels or within ethylene vinyl acetate copolymer (EVAc). The polymer is preferably delivered intra-luminally; (e) within a viral-liposome complex, such as Sendai virus; (f) as a peptide-DNA conjugate; (g) using catheters to deliver intra-luminal formulations of the nucleic acid as a solution or in a complex with a liposome; (h) catheter delivery to adventitial tissue as a solution or in a complex with a liposome; (i) the nucleic acid may be bound to a delivery agent such as a targeting moiety, or any suitable carrier such as a peptide or fatty acid molecule; (j) the nucleic acid may be delivered by a double angioplasty balloon device fixed to catheter; or (k) the nucleic acid could be delivered on a specially prepared stent of the Schatz-Palmaz or derivative type. The stent could be coated with a polymer or agent impregnated with nucleic acid that allows controlled release of the molecules at the vessel wall.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g inert diluent, preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatine and glycerin, or sucrose and acacia gum; and mouthwashes comprising the active ingredient in a suitable liquid carrier.

Compositions suitable for topical administration to the skin may comprise the compounds dissolved or suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol and water. Transdermal patches may also be used to administer the compounds of the invention.

Compositions for rectal administration may be presented as a suppository with a suitable base comprising, for example, cocoa butter, glycerin, gelatine or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include cornstarch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

In certain embodiments of the present invention there is provided an agent which inhibits promyelocytic leukemia (PML) protein for treating cancer and other hyperproliferative disorders in a subject in need thereof.

In yet further embodiments of the present invention there is provided a use of a therapeutically effective amount of an agent which inhibits promyelocytic leukemia (PML) protein for the manufacture of a medicament for treating a hyperproliferative disorder in a subject in need thereof. The skilled person will be familiar in how the medicament should be formulated for administration to a subject in need thereof. This includes the formulation disclosure provided above.

Those skilled in the art will appreciate that the invention described herein in susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Certain embodiments of the invention will now be described with reference to the following examples which are intended for the purpose of illustration only and are not intended to limit the scope of the generality hereinbefore described.

EXAMPLE 1

Methods and Materials

All materials were purchased from Sigma Chemicals Co., St. Louis, Mo., USA, unless otherwise stated. Solvents were analytical grade and water was double distilled. All experiments were performed in triplicate and repeated at least 3 times.

Cell Culture

Human colon adenocarcinoma cell lines HT29 (mutant p53(R273H); p53273), SW480 mutant p53 (R273H/P309S; $p53^{273/309}$), engineered colon carcinoma cell line HCT116 p53−/− (Bunz et al.) and breast cancer cell line SKBR3 (containing mutant p53(R175H); $p53^{175}$) and their derivatives, were cultured in Dulbecco's Modified Eagle's Medium containing 10% fetal calf serum (Biological Industries, Kibbutz Beit-Haemek, Israel). Promyelocytic leukemia cells NB4 (mutant p53(R248Q/R273H), $p53^{248/273}$) (Fleckenstein et al.), human lung adenocarcinoma cell line H1299 lacking p53 expression, and its derivatives stably expressing either mutant $p53^{273}$ or $p53^{175}$ (Blandino et al.) were grown in Roswell Park Memorial Institute (RPMI) medium supplemented with 10% fetal calf serum.

Cell lines with stably knocked-down p53 were generated by transduction using p53siRNA (Brummelkamp et al.) inserted into a retroviral vector (pRetro-SUPER) and polyclonal populations were selected with puromycin.

Knock-Down of PML

Cell lines in which PML was inducibly knocked-down were generated by co-infection with a lentivirus (pLVTHM) expressing the short hairpin RNA (shRNA) PML target sequence GACCAACAACATCTTCTGC (shPML$_1$; SEQ ID No: 1) or AGATGCAGCTGTATCCAAG (shPML$_2$; SEQ ID No: 2; Tavalai et al.) and a lentivirus expressing a tetracycline repressor (pLV-Ttrkrab-Red). Control cell lines with shLacZ and relevant wobble shPML control sequences GACCAACAATATATTCTGC (w-shPML$_1$; SEQ ID No: 4) and AGATGCAGCTGTATCCAAG (w-shPML$_2$; SEQ ID No: 5) were also generated under the control of a tetracycline repressor. PMLi to target sequence GAGTCGGCCGACTTCTGGT (SEQ ID No: 3; Bruno et al), referred to subsequently as PML$_3$i was transfected into SKBR3 cells using Lipofectamine™ 2000 (Invitrogen Corporation, Carlsbad, Calif. 92008 USA), according to the manufacturer's instructions.

Western Blot Analysis and Immunoprecipitation

Western blot analysis and immunoprecipitation assays were carried out as previously described (Louria-Hayon et al.). The antibodies used in this study were: anti-human p53 monoclonal antibodies PAb1801 and D01, anti-phospho-p53 Thr$^{18}$ polyclonal antibody (Saito et al.), anti-phospho-p53 Ser$^{20}$ polyclonal antibody (Cell Signaling Technology, Beverly, Mass., USA); anti-PML monoclonal antibody (clone PML-97; Sigma Chemical Co., St Louis, Mo., USA), anti-GFP (Roche Applied Science, Mannheim, Germany), HRP-conjugated goat anti-mouse IgG, Envision peroxidase antimouse or anti-rabbit (Dako Corp., Glostrup, Denmark). The antibodies anti-p53 goat polyclonal antibody (FL-393, AC), anti-p53 rabbit polyclonal antibody (FL-393, FC) and anti-PML polyclonal rabbit antibody ((H-238) sc-5621) were from Santa Cruz Biotechnology, Santa Cruz, Calif., USA.

Transactivation Assays

The dual luciferase assay was performed in triplicate according to the manufacture's instructions (Promega Corporation, Madison, Wis., USA). Briefly, for H1299 and its derivatives (200,000 per 3.5 cm dish) were transiently co-transfected using Polyethylenimine (PEI) with reporter constructs pCCAAT-B2LUC (Bolognese et al.) or pCCAAT-cdc25CLUC (Manni et al.) 1 μg; 6 μg of plasmid expressing PML IV or equal amount of empty vector and 0.25 ng of Renilla luciferase SV40 reporter (Promega Corporation, Madison, Wis., USA). After 48 h, the fold change in relative firefly to Renilla luciferase activity was compared between cell lines without p53 to those bearing exogenously expressed p53 mutants 273 or 175.

For LacZi-SKBR3 and PML3i-SKBR3, cells ($1.5 \times 10^5$) were transiently transfected with expression plasmids, reporter constructs, and 0.51 μg of CMV β-galactosidase plasmid (pcDNA3-β-gal vector) as an internal control for transfection efficiency. Precipitates were removed and cells were treated with 0.5 μg/ml ADR for 48 hr. Luciferase activity was assayed on whole-cell extract, as described (Manni et al.). The luciferase values were normalized to β-galactosidase activity and protein content.

Flow Cytometry Analysis of Live Cells

Cells were cultured in the absence or presence of doxycyclin (0.2 μg/ml added every second day) for three days then 25,000 cells were plated (with doxycyclin maintainance in culture for continued shRNA induction) and harvested at selected time points. Cells adherent to the plate were released with trypsin-EDTA and combined with those suspended in the culture supernatant prior to flow cytometric analysis of live cell numbers, as discriminated by propidium iodide exclusion using a cell sorter (FACSCalibur) harnessed to CellQuest software (BD Biosciences; San Jose, Calif., USA).

Colony Formation Assay

Cancer cell lines were plated (700 per well) in 5 cm diameter dishes in the absence or presence of tetracycline (0.2 μg/ml added every second day) for 21 days. At harvest the cells were fixed in ethanol and stained in 0.1% crystal violet.

MTT Metabolic Assay

Cells either untreated or treated with doxycyclin (0.2 μg/ml) to knock down PML were plated 4000 per well in a 96 well plate and allowed to recover for 24 h. 3-(4,5-Dimethylthiazolyl-2)-2,5-diphenyltetrazolium bromide (MTT, 0.5 μg/ml final concentration) was added to the wells and the experiment was terminated after an additional 4 h incubation, by aspiration of the liquid and addition of 200 μl of DMSO.

The absorbance was read at 540 nm, relative to a reference wavelength of 630 nm (Mosmann et al.).

BRDU

Cells were plated $2 \times 10^6$/10 cm dish and allowed to recover 24 h. BRDU was incorporated (20 µM, 4 h), prior to cell harvest with trypsin-EDTA and fixation in 70% methanol, −20° C. overnight. BRDU detection was undertaken subsequent to sequential rehydration in HCl(2N)/Triton-X(0.5%) then incubation in Boric acid (0.1M), anti-DRDU FITC antibody (BD Biosciences; San Jose, Calif., USA) in PBS/BSA (1%)/Triton-X(0.5%). DNA was labeled using propidium iodide 0.5 mg/ml and incorporation was analyzed using the FACs calibur (BD Biosciences; San Jose, Calif., USA)

RT-PCR Analysis

Cellular RNA was isolated by Tri-Reagent (MRC Inc.; Cincinnati, Ohio, USA) using the manufacture's instructions, DNA was removed from the samples using DNase treatment (DNA-free kit, Ambion Applied Biosystems; Foster City, Calif., USA), cDNA was synthesized from the purified RNA using M-MLV Reveres Transcription kit (Promega, Madison, Wis., USA). Primers for ribosomal 18S were forward: CTACCACATCCAAGGAAGGC (SEQ ID No: 6); and reverse: AAGAATTTCACCTCTAGCGGC (SEQ ID No: 7). Primers for PML were forward: CGCCCTGGATAACGTCTTT (SEQ ID No: 8) and reverse: ACTGTGGCTGCTGTCAAGG (SEQ ID No: 9).

Immunofluorescent Staining Analysis

For immunofluorescent staining, cells were plated on coverslips. 24 hrs later, cells were washed and fixed with 3.7% paraformaldehyde, and permeabilized with 0.2% Triton X-100. p53 was visualized with the simultaneously exposure of DO1 and 1801 antibodies in conjunction with goat anti-mouse FITC conjugated secondary antibody (Jackson ImmunoResearch Laboratories Inc., West Grove, Pa., USA). PML was detected using anti-PML polyclonal antibody rhodamine conjugate (PG-M3 TRITC; sc-966; Santa Cruz Biotechnology, Santa Cruz, Calif., USA). Proteins were visualized by confocal fluorescence microscopy using a Zeiss 410 microscope, (PlanApochromat x40), and Olympus FV1000 microscope, ×60, using Fluview1000 v.1.5 software.

EXAMPLE 2

Mutant p53 and PMI Interact and Co-Localize

Figure 7:
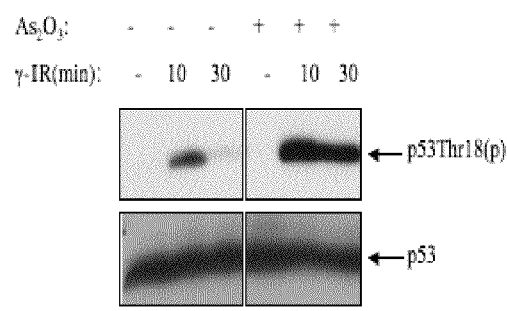
FIG. 7 shows activation of PML by arsenic trioxide (As$_2$O$_3$) facilitated IR-induced phosphorylation of p53 on Thr18 [p53Thr18(p)] in NB4 cells. As indicated, NB4 cells were treated with As$_2$O$_3$ (1 μM, 4 h) and γ-IR (5Gy) and harvested either 0, 10 or 30 minutes post IR exposure. After SDS-PAGE, samples were subjected to immunoblotting using anti-phopho-p53Thr18 antibody, followed by anti-p53 antibodies (DO1 and 1801 monoclonal antibodies).

The inventors have previously shown that PML facilitates the phosphorylation of wt p53 at $Ser^{20}$ by check-point kinase 2 (Chk2; Louria-Hayon et al.) and $Thr^{18}$ by CK1 (Alsheich-Bartok et al.). These observations raised the surprising possibility that PML may also facilitate the phosphorylation of mutant p53. To investigate this suggestion, NB4 acute promyelocytic leukemia cells were exposed to ionizing irradiation in order to induce p53 phosphorylation in the absence of active PML, or in the presence of arsenic trioxide ($As_2O_3$) which activates PML. Consolidating previous findings (Alsheich-Bartok et al.), activation of PML by $As_2O_3$ facilitated IR-induced phosphorylation of p53 on $Thr^{18}$ (FIG. 7), suggestive of PML involvement.

Wt p53 and PML (isoform IV, formerly PML3) interact and co-localize (Fogal et al.) upon exposure to stress (Louria-Hayon et al. and Bischof et al.). The observed PML-mediated phosphorylation of mutant p53 provoked the notion that mutant p53 and PML may also interact and co-localize. To examine for PML and mutant p53 interaction, the following mutant p53 expressing cell lines were studied: HT29 ($p53^{273}$), SW480 ($p53^{273/309}$) and SKBR3 ($p53^{175}$). As controls, the wt p53 expressing cell lines MCF7 and HCT116 were studied. Genotoxic stress was induced either by exposure to UV light (40 µJ×100), or by treatment with doxorubicin (2 µg/ml, 1 h) as indicated. Extracts from mutant p53 bearing cells were sequentially subjected to co-immunoprecipitation (co-IP) using anti-p53 antibodies (FL393 goat) followed by PML blotting (FIGS. 1A(i)-(iii)). Conversely, due to low endogenous p53, extracts of wt p53 expressing cells were immunoprecipitated with anti-PML antibodies prior to p53 blotting (FIGS. 1A(iv)-(v)). This analysis revealed a temporally distinct interaction between PML and mutant or wt p53 respectively. Mutant p53 was identified to be associated with PML in the absence of additional external genotoxic stress. In contrast, wt p53 association with PML was enhanced in a time dependent manner subsequent to UV exposure. This increase correlates well with the increase in wt p53 levels.

Figure 1B:
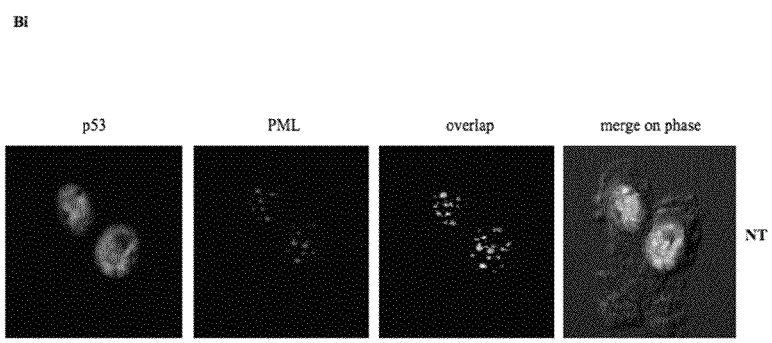
Figure 1C:
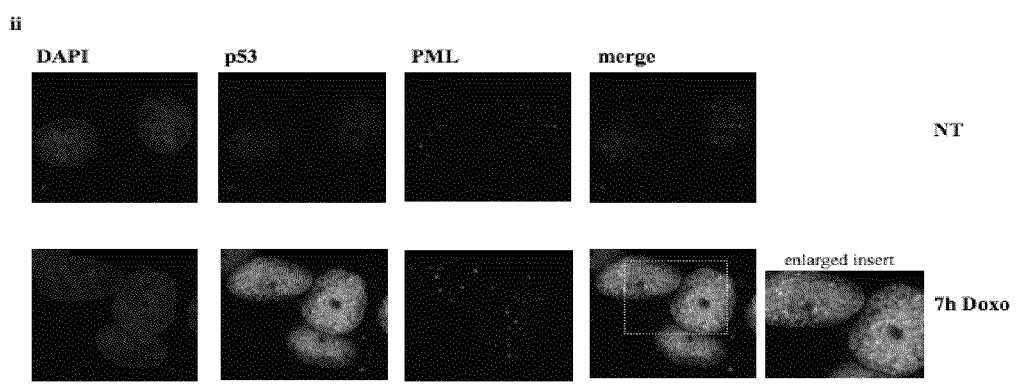
Figure 8:
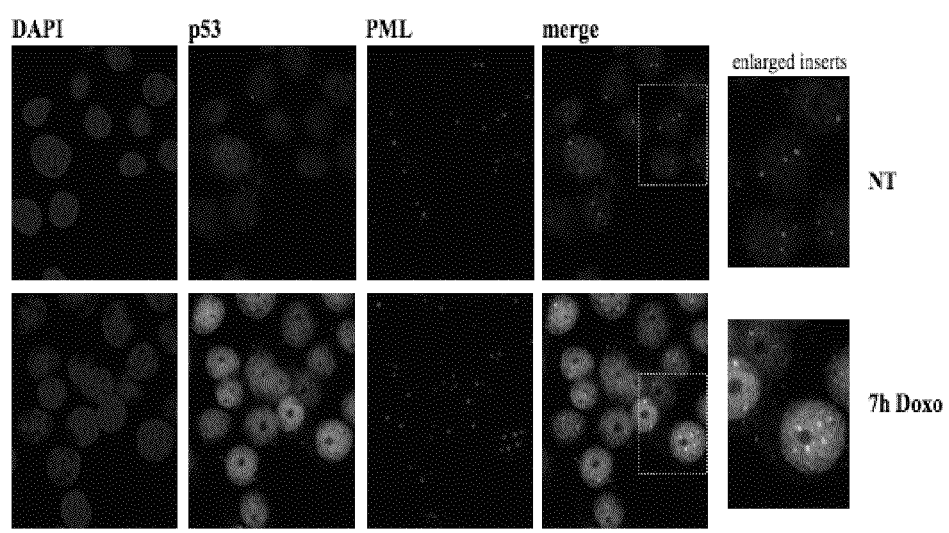
FIG. 8 shows RKO cells bearing wtp53 were plated on coverslips and 24 h subsequently were alternatively either left untreated, or exposed to doxorubicin (2 μg/ml for 1 h, washed out and harvested after an additional 6 h). Fixed cells were stained with anti-PML polyclonal antibodies in conjunction with Cy5-conjugated secondary antibody (red) and p53 monoclonal antibodies followed by Cy2-conjugated secondary antibody (green).

Given the interaction between PML and mutant p53, the possible co-localization of the two proteins in SW480 was examined using immunofluorescence staining. Critically, localization of endogenous mutant p53 and PML was detected in these cells. By studying these proteins at endogenous levels avoids the phenomena that transfected proteins often co-localize with PML in the PML-NBs due to their overexpression. Stained cells were analyzed by confocal microscopy (FIG. 1B). While mutant p53 appears to be expressed throughout the nucleus, PML was localized to the PML-NBs. The inventors therefore analyzed the extent of co-localization (using the FluView 1000 v.1.5 software) from the perspective of PML, and identified a significant extent of co-localization of mutant p53 (~10%). This observation that without additional exogenous stress, mutant p53 interacts with PML and co-localizes with it in the PML-NBs (FIG. 1B), is reminiscent of the interaction of genotoxically stressed wt p53 with PML, as observed with MCF7 cells stressed with doxorubicin (FIG. 1C) and RKO (FIG. 8).

EXAMPLE 3

Knockdown of PML Reduces the Number of Mutant P53 Bearing Cancer Cells

Figure 2:
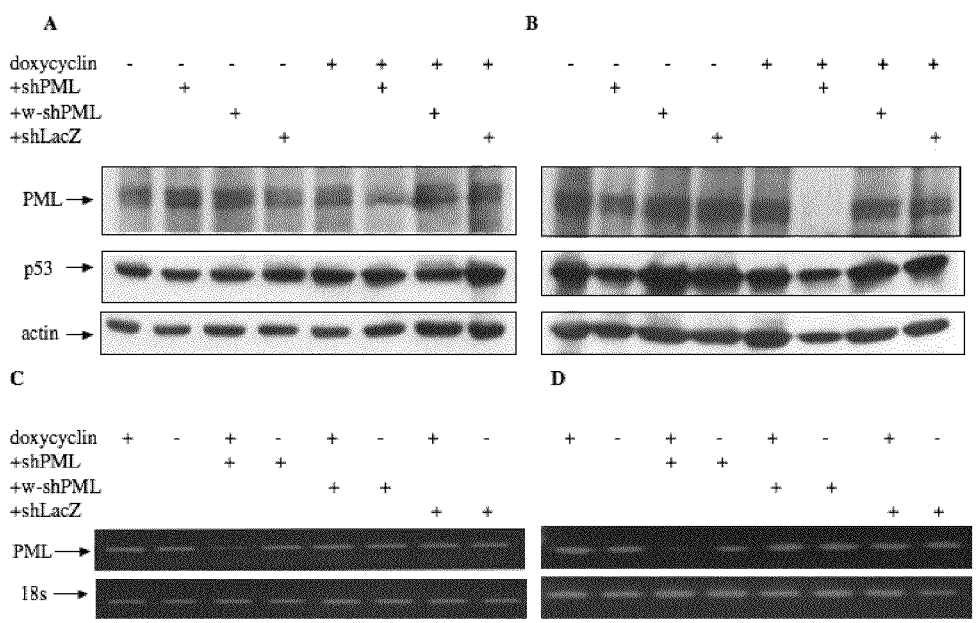
FIG. 2 shows knockdown of major PML isoforms was achieved with shRNA technology. Cell lines HT29 (A) and SW480 (B) either nontransduced or transduced with shPML$_1$, w-shPML$_1$, or shLacZ were exposed to doxycycline for 72 h for PML knockdown as indicated. Immunoblotting was performed with anti-PML (Sigma Chemicals), anti-p53 (DO1 and 1801), and anti-actin monoclonal antibodies. RT-PCR examination of these cell lines corroborated the reduction in PML in these HT29 and SW480 cells (C and D, respectively), in which PML levels were normalized to 18 s.

To assess the influence of PML in human cancer cell lines bearing endogenous mutant p53, PML expression was knocked down using RNA interference. HT29 and SW480 were transduced with lentivirus encoding shRNA to PML. The efficacy of PML down-regulation was evaluated by Western blotting using an antibody that detects multiple PML isoforms (clone PML-97; Sigma). Under the influence of $shPML_1$ (SEQ ID No: 1) expression of major PML isoforms was reduced in HT29 and SW480 (FIGS. 2A and 2B, respectively). Control shRNA to LacZ (shLacZ) and wobble shRNA to PML (w-$shPML_1$; SEQ ID No: 4), failed to reduce PML levels, indicating the specificity of PML knock-down. A reduction in PML levels in response to $shPML_1$ was also confirmed at the mRNA level. RT-PCR directed to a region common to multiple isoforms of PML revealed a reduction in PML transcript, consistent with the results observed at the protein level (FIGS. 2C and D). PML knock down did not influence the p53 RNA levels in these cells (data not shown).

Figure 3G:
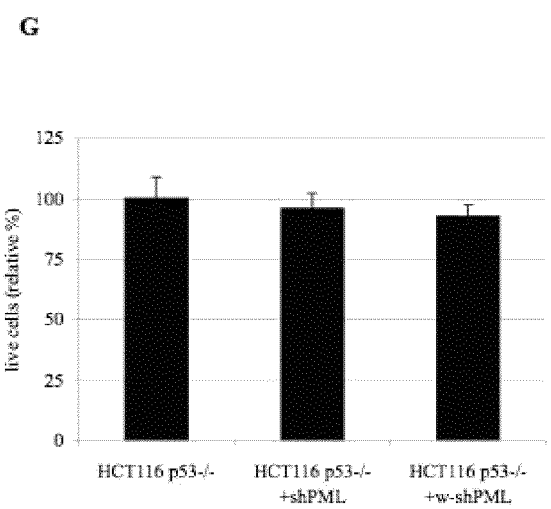
FIG. 3 shows knockdown of PML inhibited cell proliferation in mutant p53 cell lines. Cell proliferation decreased in HT29 (A) and SW480 (B) cells when subjected to PML knockdown (induced with doxycycline exposure) for 7 or 8 d, as identified using flow cytometry to distinguish propidium-negative live cells. Colony formation was significantly impaired in HT29 (graphed in (C), with representative plates shown in (E)) and SW480 (graphed in (D), with representative plates in (F)) cells subjected to doxycycline-induced PML knockdown for 21 d. (G) In contrast, HCT116 p53−/− cells were not growth-inhibited by PML knockdown as assessed by flow cytometry of the propidium iodide-excluded live cell population, 8 d after transduction: HCT116 p53−/− not transduced (column 1), transduced for shPML$_2$ without repressor (column 2), or w-shPML$_2$ without repressor (column 3).
Figure 9:
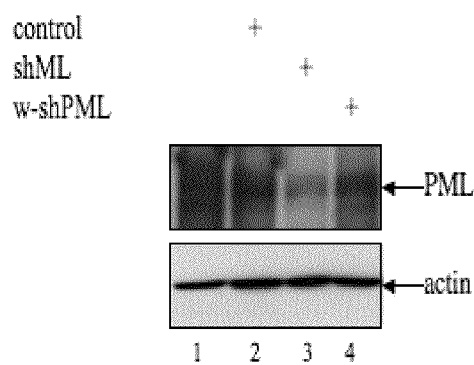
FIG. 9 shows shPML induced PML knock-down in HCT116 p53−/−. Cells were either not transduced (lane 1) or transduced with the repressor construct alone (control; lane 2), the shPML$_2$ without repressor (lane 3) or w-shPML$_2$ without repressor (lane 4). Immunoblotting was performed with anti-PML (Sigma) and anti-actin antibodies.

The influence of PML knock down on the growth of HT29 and SW480 was examined. $shPML_1$ (SEQ ID No: 1) was induced by growing the cells in the presence of doxycyclin. Live cell numbers were measured at selected time intervals by flow cytometry. Dead cells were excluded using propidium iodide (PI) staining. Down regulation of PML (induced by 7 or 8 days of doxycyclin exposure) significantly reduced the number of live cells in HT29 and SW480 cultures (FIGS. 3A and 3B, respectively). Further confirmation of the influence of PML down regulation was provided with $shPML_2$ (SEQ ID No: 2) in HT29 and SW480, where similar results to those using shPML₁ (SEQ ID No: 1) in FIG. 3 were recorded (data not shown). Depletion of endogenous mutant p53 has been shown to reduce colony formation competence (Bossi et al.) whereas over-expression of mutant p53 proteins in p53-null cells was shown to enhance plating efficiency (Blandino et al., Shaulsky et al., Dittmer et al. and Cadwell et al.). The inventors therefore measured the effect of PML depletion on colony formation of the mutant p53 cell lines HT29 and SW840 (FIGS. 3C and 3D, respectively; with representative plates in FIGS. 3E and F). PML knockdown in HT29 almost completely blocked colony formation (>90% inhibition), and SW840, >70% inhibition was observed. This result is consistent with PML knockdown reducing cancer cell numbers. Importantly, down regulation of PML (for 8 days) in cells lacking p53, HCT116 p53−/− (FIG. 9) had no significant effect on their proliferation (FIG. 3G), demonstrating that the observed effect on growth was dependent on mutant p53.

Figure 4A:
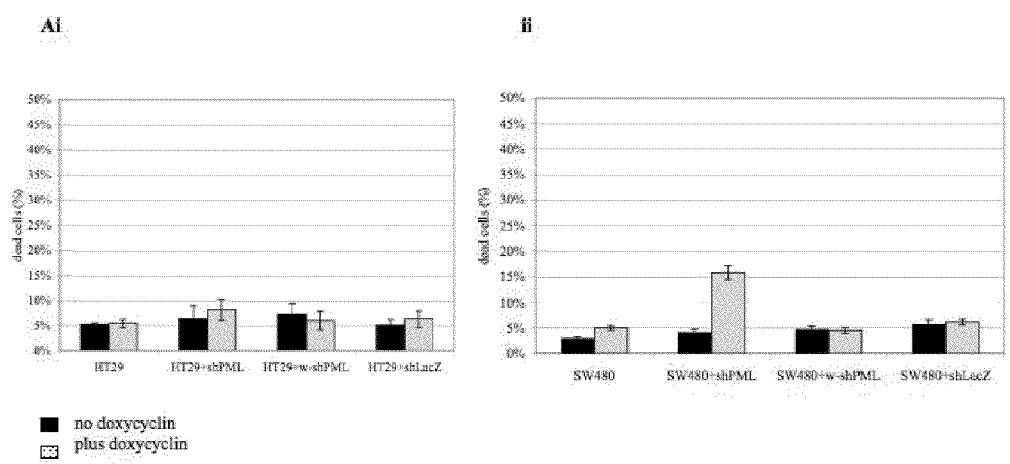
FIG. 4 shows knockdown of PML affects cell cycle progression in a mutant p53-dependent manner, with only a modest effect on cell death or metabolism. (A) knockdown of PML induced little additional cell death in the mutant p53-bearing lines HT29 and SW480, as assessed with propidium iodide exclusion using flow cytometric analysis. shPML expression was induced by doxycycline exposure in HT29 (for 7 d; (i)) and SW480 (for 8 d; (ii)). (B) MTT metabolic assay of HT29 cells transformed with either shPML$_1$ or w-shPML$_1$ and exposed to doxycycline (0.2 μg/mL) over a period of 3, 4, or 11 d, exhibited only a minor reduction in metabolic activity in response to PML knockdown when cells were plated (4,000 cells per 96 wells) 24 h prior to each assay time point. (C) sustained PML knockdown in HT29 cells (involving 8 d of doxycycline induction of shPML$_1$) selectively reduced the cell cycle S phase and perturbed G$_1$ and G$_2$ in HT29 cells, as compared with either nontransduced or w-shPML$_1$ controls, identified through flow cytometric analysis of BrdUrd incorporation. (D) knockdown of PML and p53 significantly increased G$_2$ in H1299-expressing exogenous mutant p53$^{175}$ cells.

Two possible explanations were envisaged for these reductions in viable cell numbers: these included a greater susceptibility to cell death, or a reduced rate of proliferation. To test the first possibility, the numbers of dead HT29 and SW480 cells were measured in the presence of shPML₁ (SEQ ID No: 1) and shPML₂ (SEQ ID No: 2) or controls. Flow cytometric analysis using propodium iodide exclusion revealed a modest increase in cell death after 7 or 8 days of PML down regulation for HT29 and SW480 (FIGS. 4A(i) and (ii), respectively).

Figure 4D:
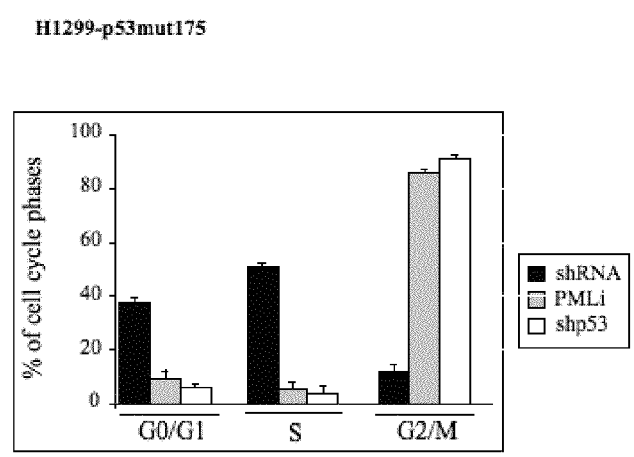
Figure 10:
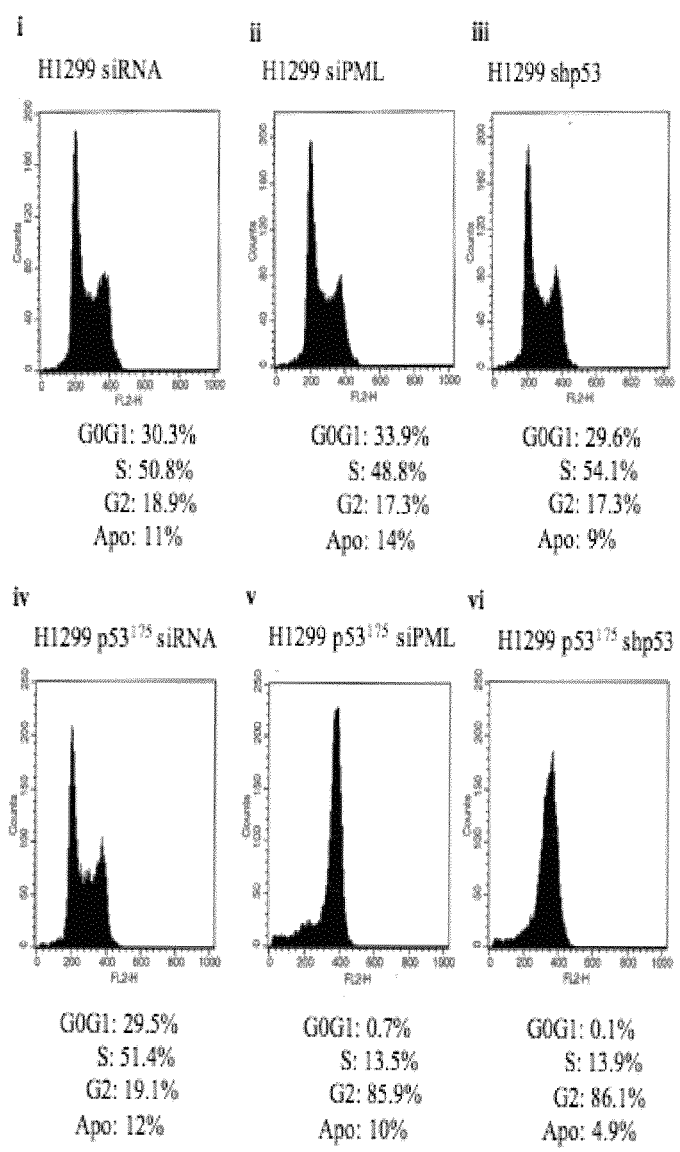
FIG. 10 shows knockdown of PML (ii) and p53 (iii) did not influence the cell cycle distribution of H1299 p53 null cells relative to the control (i) as assessed by flow cytometry. In contrast, knockdown of PML (v) and p53 (vi) significantly increased G2 in H1299 expressing exogenous mutant p53$^{175}$ cells, relative to the control (iv).

To ascertain the influence of PML levels on the proliferation of HT29 human cancer cells, they were subjected initially to metabolic evaluation using an MTT assay and cell cycle analysis using BrdUrd incorporation. MTT analysis revealed a slightly lower rate of metabolism in HT29 cells expressing shPML₁ (SEQ ID No: 1) as compared with control w-shPML₁ (SEQ ID No: 4; FIG. 4B), after 3, 4 and 11 days of doxycycline exposure. This reduction was consistent with the reduced growth rate, but cannot explain the marked difference in cell numbers. It is important to clarify that because the MTT assay involved plating cells of equal number 24 hours in advance of each assay time point, there was continual selection for live cells, which is likely to have masked the accrued effects detected with longer-term plating for the flow cytometric analysis and the colony assay. After 3 days of doxycyclin induction, the relative number of cells cycling through the S-phase was comparable for the parental line and those expressing w-shPML₁ (SEQ ID No: 4) and shPML₁ (SEQ ID No: 1), as assessed by BrdDUrd incorporation, with a slightly higher level of G1 and a lower level of G2 for cells expressing shPML₁ (SEQ ID No: 1; data not shown). Significantly, after 8 days of continuous PML knock down, the level of BrdUrd incorporation into the S-phase was reduced markedly, with corresponding increases in G1 and G2 (FIG. 4C). To further substantiate the mutant p53 dependence of cell cycle perturbation induced through PML knockdown, H1299 cells either without, or bearing mutant p53¹⁷⁵, were subjected to cell cycle analysis and flow cytometry (FIG. 10). Although the cell cycle profile of p-53 null H1299 cells exposed to either control siRNA vector, PML₃ i (SEQ ID No: 3) or siRNA to p53 were not disrupted; a striking increase in G₂ was shown in response to either PMLi or shp53 (GACTCCAGTGGTAATCTA; SEQ. ID No: 10) in the mutant p53 context (FIG. 4D). This data further substantiates the observed PML dependence of mutant p53-bearing cancer cells for cell cycle progression (as seen for HT29 in FIG. 4C).

EXAMPLE 4

PML IV Enhances the Transcriptional Activity of Mutant p53

Figure 5C:
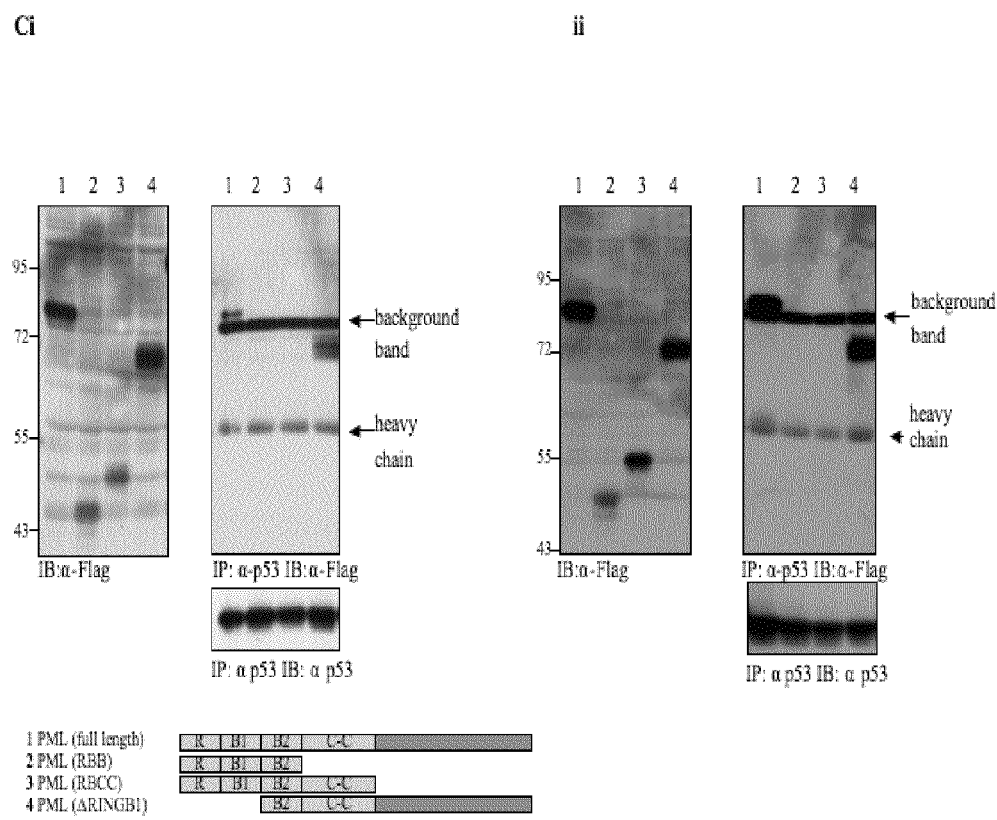
FIG. 5 shows PML IV promoted mutant p53 transcriptional activation in H1299 cells exogenously expressing either mutant p53$^{273}$ or p53$^{175}$, and was identified to interact with mutant p53 through its COOH terminus. H1299, null for p53, exogenously expressing either mutant p53$^{273}$, or p53$^{175}$ were compared for their effect on pCCAAT-B2LUC (A) or pCCAAT-cdc25CLUC (B). Renilla was cotransfected either in the absence or presence of PML and after 48 h, expression was assessed. Mean of triplicate determinations representative of at least three separate experiments; bars, SD. (C) H1299 cells were transfected with PML deletion mutants (1-4 as schematically presented) together with mutant p53$^{273}$ (i) or p53$^{175}$ (ii). 24 hours after transfection, p53 was immunoprecipitated from the cell extracts using goat polyclonal anti-p53 antibody followed by immunoblotting with anti-Flag antibody to detect PML Flag-tagged proteins.

At what level PML benefits the survival of these mutant p53 bearing cancer cell lines was the next obvious question. PML has been shown to enhance the transcriptional activity of wt p53 (Louria-Hayon et al.). Because mutant p53 has transcriptional activity (Strano et al. and Di Agostino et al.) it was of interest to examine whether PML IV (the isoform identified to interact with wt p53; Bischof et al.) influences this activity of mutant p53. For this purpose we employed a luciferase reporter assay in a p53 deficient H1299 lung carcinoma cells to measure the effect of PML-IV (referred to as PML hereafter) on the activation of a number of well characterized transcriptional targets of mutant p53 (Di Agostino et al.). Parental and H1299 cells stably expressing exogenous p53 mutants (R273H and R175H) were transfected with luciferase reporter plasmid under the control of cyclin B2 or Cdc25C promoters. In contrast to the known repression of cyclin B2 by wt p53 (Manni et al. and data not shown), p53 R175H mutant induced the cyclin B2 promoter, consistent with previous studies (Di Agostino et al.; FIG. 5A). In this assay p53 R273H mutant had no major effect on this promoter as previously reported (Di Agostino et al.). Strikingly however, inclusion of PML enhanced the reporter activity of this promoter under the influence of both these p53 mutants. Similarly, expression of PML enhanced the induction of the Cdc25C promoter (FIG. 5B). It should be noted that expression of PML alone also enhanced the activity of this promoter in a mutant p53-independent manner by an unknown mechanism. Nevertheless, these results show that expression of PML enhances the transcriptional activity of at least 2 forms of mutant p53.

To define the nature of interaction between mutant p53 and PML, PML IV domain mutants bearing a Flag-tag were transfected together with either mutant $p53^{273}$ or $p53^{175}$ into H1299 can co-immunoprecipitations were performed by immunoprecipitating using anti-p53 and immunoblotting using anti-Flag antibody. The PML IV carboxyl-terminus was identified as the region interacting with the p53 mutants (FIG. 5C(i) and (ii), respectively)

EXAMPLE 5

Figure 6A:
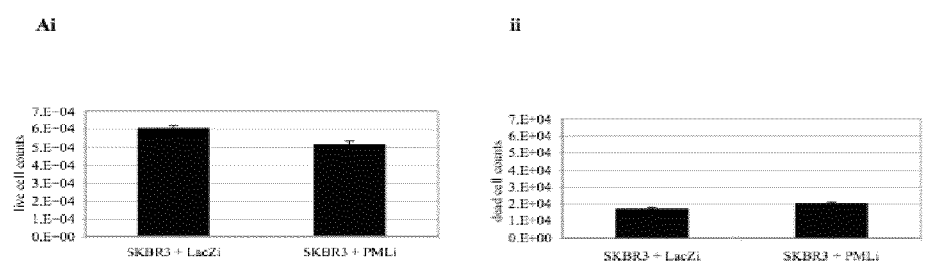
FIG. 6 shows PML knockdown in SKBR3 under the influence of genotoxic stress, had only a modest effect on cell proliferation and viability, but suppressed mutant p53 transcriptional target activation. Knockdown of PML using siRNA in SKBR3, in conjunction with Adriamycin exposure (0.5 μg/mL; 24 h), slightly reduced SKBR3 live cell numbers, without significant cell death. (A) live cells under the influence of either LacZi or PMLi (i), were differentiated from dead cells (ii), using trypan dye exclusion. (B) knockdown of endogenous PML or mutant p53 in genotoxically stressed SKBR3 cells suppressed the activation of mutant p53 transcriptional targets in luciferase reporter constructs pCCAAT-B2LUC (i) or pCCAAT-cdc25CLUC (ii). SKBR3 were transfected with either LacZi, sip53, or PML$_3$i simultaneously with β-galactosidase vector and luciferase reporter constructs, subsequently after 16 h, cells were then exposed to Adriamycin (0.5 mg/mL for 24 h). Luciferase activity was normalized to β-galactosidase activity and protein content. Knockdown of endogenous PML or mutant p53 in genotoxically stressed SKBR3 cells reduced RNA expression of endogenous cyclin B and Cdc25C (C). SKBR3 cells were transfected with either LacZi, sip53, or PML$_3$i prior to Adriamycin (0.5 mg/mL; 24 h) treatment and subsequent RNA extraction and RT-PCR analysis.

Down Regulation of PML Reduces the Growth of Cells Expressing Mutant p53 in Response to Genotoxic Stress Expression of certain p53 mutants confers cells with some resistance to genotoxic stress (Strano et al.). It was therefore important to define whether PML contributes to this biological effect of mutant p53. To this end PML expression was down regulated in SKBR3 cells and cells were exposed to 0.5 µg/ml Adriamycin for 24 h. The effect on cell survival was determined by Trypan blue dye exclusion. Down regulation of PML reduced the numbers of live cells (FIG. 6A(i)), whereas no significant increase in cell death was identified (FIG. 6A(ii)). Importantly, this reduction in cell numbers did not correspond to a significant increase in cell death, (consistent with short term PML down regulation in HT29 and SW480 (FIG. 4A(i) and (ii), respectively).

Figure 6B:
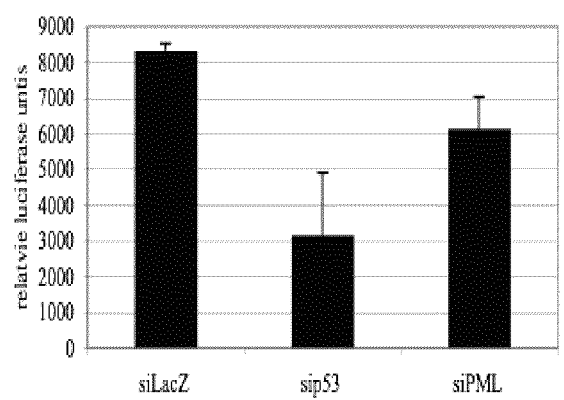
Figure 6B:
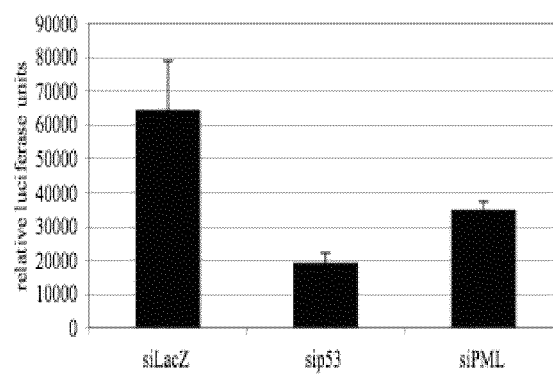
Figure 6C:
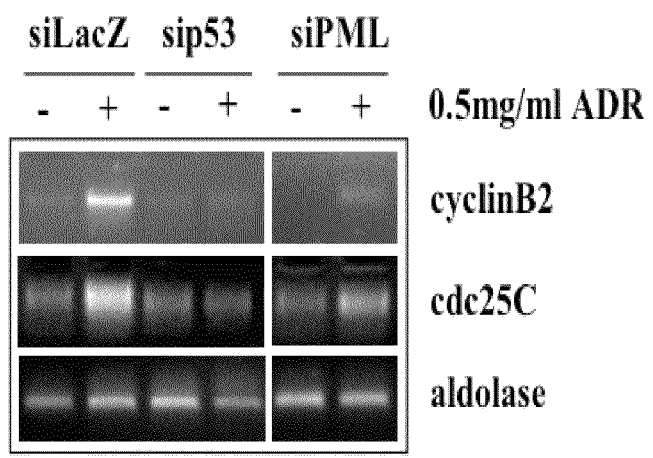

In addition, the effect of PML down-regulation on the transcription of the mutant p53 targets cyclin B2 and Cdc25C, in response to genotoxic stress, was examined in the endogenous mutant p53¹⁷⁵ background of SKBR3 cells. SKBR3 cells were transfected with either PML3i (SEQ ID No: 3) or shp53 (GACTCCAGTGGTAATCTA; SEQ ID No: 10), and luciferase reporter constructs for either Cyclin B2 or Cdc25c. After 24 hours, the cells were exposed to adriamycin (0.5 µg/ml). Down regulation of p53 suppressed the induction of both promoters (FIG. 6B(i) and (ii), respectively). Strikingly, down regulation of PML also reduced Cyclin B2 and Cdc25C promoter activity (FIGS. 6B(i) and (ii), respectively). The suppression of endogenous cyclin B2 and Cdc25C in response to either p53 or PML down-regulation, under the influence of Adriamycin, was also confirmed at the RNA level by RT-PCR (FIG. 6C). Together these results strongly support a role for PML in the transcriptional activity of mutant p53.

Discussion

The present inventors have made the surprising discovery that PML not only acts as an activator of wt p53 but also as an activator of mutant p53.

Wt p53 can lose its tumor suppressive reflex to stress exposure through substitutions of specific single amino acids, some of which can confer gain of function properties (reviewed by Strano et al.). Intriguingly, despite differences between wt and mutant p53 protein conformation, stability and diametrically distinct effects on cell growth and survival, they appear to share some aspects of their regulation. The present inventors demonstrate a physical and functional link between PML and mutant p53. PML interacts and co-localizes with mutant p53 (FIG. 1). Although the same region of PML interacts with wt and mutant p53 (FIG. 5C), the pattern of interaction differs markedly. Whereas the interaction between PML and wt p53 occurs in response to DNA damage, (in correlation with increased p53 expression, (FIGS. 1Aiv and v), PML interaction with mutant p53 in tumor cells occurs in the absence of genotoxic stress (FIGS. 1Ai-iii). This suggests that oncogenic and oxidative stress in the tumour cell may suffice to trigger PML-mutant p53 interactions.

Mutant p53, in cooperation with NF-Y, transcriptionally activates a number of cell cycle genes, such as cyclin B2 and cdc25c, which have been proposed to contribute to a gain of function by mutant p53 (Di Agostino et al.). These genes are repressed by wt p53 (Manni et al., Imbriano et al. and St Clair et al.). Intriguingly, the induction of these target promoters was augmented by exogenous expression of PML, and their expression was reduced by down regulating PML expression (FIGS. 5 and 6, respectively). These findings raised the surprising possibility that PML may promote mutant p53 gain of function.

The inventors found that PML is critical for the proliferation of tumour cells expressing mutant p53 (FIG. 3). Temporal down regulation of PML expression reduced cell numbers by reducing the number of cells in S-phase and increasing the proportion of cells in G1 and G2 cell cycle arrest, and was associated with a modest induction of cell death after extended shPML induction (FIG. 4). Strikingly, down-regulation of PML blocked the ability of HT29 and SW480 cells to form colonies (FIG. 3). In marked contrast, down regulation of PML had no effect on the proliferation of cells lacking p53 (HCT116 p53−/−; FIG. 3), or of cultured human foreskin fibroblasts (HFFs) expressing wt p53 (Everett et al.). Furthermore, PML deficient mice are viable and develop normally. Embryo fibroblasts derived from these mice exhibit no growth impairment, and appear to grow even faster than control cells (Gurrieri et al.). Therefore, these results suggest that the growth inhibitory effects induced by down-regulation of PML expression are mutant p53 context dependent.

In stark distinction, overexpression of PML is lethal in normal cells (Quignon et al.). Specifically, PML isoform IV, which interacts with p53, induces apoptosis (Xu et al.). Critically, PML overexpression is growth inhibitory to cancer cells with wild type, mutant (Trecca et al.) and without functional p53 (Li et al.). Elevated PML expression perturbs the cell cycle (Trecca et al. and Li et al.). Thus, there is a differential response to PML manipulation, where normal cells with wt p53 can tolerate its reduction, but not elevation, while mutant p53 cancer cells are disrupted by both PML overexpression and knock down.

Normal PML expression is critical for the growth of tumor cells bearing mutant p53. This conclusion is supported by several clinical observations. This conclusion is supported by several clinical observations. Patients with acute promyelocytic leukemias, expressing PML-RARa oncogenic fusion (Salomoni et al.) rarely contain p53 mutations (Longo et al. and Trecca et al.). Furthermore, PML is commonly down regulated in breast and prostate cancer, where p53 mutations are less frequent (Alseich-Bartok et al.). Additional analyses are required to substantiate this apparent correlation. The findings presented in the Examples above suggest that deregulation of PML and p53 mutations are incompatible with tumour development. The differential impact of PML reduction on the growth of cancer cells expressing wt or mutant p53 suggests a selective therapeutic opportunity that could be exploited to target mutant p53 bearing tumors.

REFERENCES

1. Alsheich-Bartok O, Haupt S, Alkalay-Snir I, Saito S, Appella E, Haupt Y. PML enhances the regulation of p53 by CK1 in response to DNA damage. Oncogene 2008; 27(26):3653-61.
2. Blandino G, Levine A J, Oren M. Mutant p53 gain of function: differential effects of different p53 mutants on resistance of cultured cells to chemotherapy. Oncogene 1999; 18(2):477-85.
3. Bischof O, Kirsh O, Pearson M, Itahana K, Pelicci P G, Dejean A. Deconstructing PML-induced premature senescence. Embo J 2002; 21(13):3358-69.
4. Bode A M, Dong Z. Post-translational modification of p53 in tumorigenesis. Nat Rev Cancer 2004; 4(10):793-805.
5. Bolognese F, Wasner M, Dohna C L, et al. The cyclin B2 promoter depends on NF-Y, a trimer whose CCAAT-binding activity is cell-cycle regulated. Oncogene 1999; 18(10):1845-53.
6. Bossi G, Lapi E, Strano S, Rinaldo C, Blandino G, Sacchi A. Mutant p53 gain of function: reduction of tumor malignancy of human cancer cell lines through abrogation of mutant p53 expression. Oncogene 2006; 25(2):304-9.
7. Brummelkamp T R, Bernards R, Agami R. A system for stable expression of short interfering RNAs in mammalian cells. Science 2002; 296(5567):550-3.
8. Bruno S, Ghiotto F, Fais F, et al. The PML gene is not involved in the regulation of MHC class I expression in human cell lines. Blood 2003; 101(9):3514-9.
9. Bunz et al. (1999) Disruption of p53 in human cancer cells alters the responses to therapeutic agents *J. Clin. Invest.* 104:263-269.
10. Cadwell C, Zambetti G P. The effects of wild-type p53 tumor suppressor activity and mutant p53 gain-of-function on cell growth. Gene 2001; 277(1-2):15-30.
11. Di Agostino S, Strano S, Emiliozzi V, et al. Gain of function of mutant p53: the mutant p53/NF-Y protein complex reveals an aberrant transcriptional mechanism of cell cycle regulation. Cancer Cell 2006; 10(3):191-202.
12. Dittmer D, Pati S, Zambetti G, et al. Gain of function mutations in p53. Nat Genet. 1993; 4(1):42-6.
13. Everett R D, Rechter S, Papior P, Tavalai N, Stamminger T, Orr A. PML contributes to a cellular mechanism of repression of herpes simplex virus type 1 infection that is inactivated by 'CPO. J Virol 2006; 80(16):7995-8005.
14. Fleckenstein D S, Uphoff C C, Drexler H G, Quentmeier H. Detection of p53 gene mutations by single strand con- 14. formational polymorphism (SSCP) in human acute myeloid leukemia-derived cell lines. Leuk Res 2002; 26(2):207-14.
15. Fogal V, Gostissa M, Sandy P, et al. Regulation of p53 activity in nuclear bodies by a specific PML isoform. Embo J 2000; 19(22):6185-95.
16. Guo A, Salomoni P, Luo J, et al. The function of PML in p53-dependent apoptosis. Nat Cell Biol 2000; 2(10):730-6.
17. Gurrieri C, Capodieci P, Bernardi R, et al. Loss of the tumor suppressor PML in human cancers of multiple histologic origins. J Natl Cancer Inst 2004; 96(4):269-79.
18. Imbriano C, Gurtner A, Cocchiarella F, et al. Direct p53 transcriptional repression: in vivo analysis of CCAAT-containing G2/M promoters. Mol Cell Biol 2005; 25(9):3737-51.
19. Iwakuma T, Lozano G. Crippling p53 activities via knock-in mutations in mouse models. Oncogene 2007; 26(15): 2177-84.
20. Izquierdo et al. Short interfering RNAs as a tool for cancer gene therapy. *Cancer Gene Therapy* 12 (3) 217-27, 2005.
21. Lang G A, Iwakuma T, Suh Y A, et al. Gain of function of a p53 hot spot mutation in a mouse model of Li-Fraumeni syndrome. Cell 2004; 119(6):861-72.
22. Lavin M F, Gueven N. The complexity of p53 stabilization and activation. Cell Death Differ 2006; 13(6):941-50.
23. Li Y, Guessous F, Kwon S, et al. PTEN has tumor-promoting properties in the setting of gain-of-function p53 mutations. Cancer Res 2008; 68(6):1723-31.
24. Longo L, Trecca D, Biondi A, et al. Frequency of RAS and p53 mutations in acute promyelocytic leukemias. Leuk Lymphoma 1993; 11(5-6):405-10.
25. Louria-Hayon I, Grossman T, Sionov R V, Alsheich 0, Pandolfi P P, Haupt Y. The promyelocytic leukemia protein protects p53 from Mdm2-mediated inhibition and degradation. J Biol Chem 2003; 278(35):33134-41.
26. Manni I, Mazzaro G, Gurtner A, et al. NF-Y mediates the transcriptional inhibition of the cyclin B1, cyclin B2, and cdc25C promoters upon induced G2 arrest. J Biol Chem 2001; 276(8):5570-6.
27. Meulmeester E, Jochemsen A G. p53: a guide to apoptosis. Curr Cancer Drug Targets 2008; 8(2):87-97.
28. Mosmann T. Rapid colorimetric assay for cellular growth and survival: application to proliferation and cytotoxicity assays. J Immunol Methods 1983; 65(1-2):55-63.
29. Olive K P, Tuveson D A, Ruhe Z C, et al. Mutant p53 gain of function in two mouse models of Li-Fraumeni syndrome. Cell 2004; 119(6):847-60.
30. Prives C, White E. Does control of mutant p53 by Mdm2 complicate cancer therapy? Genes & Dev 2008; 22(10): 1259-64.
31. Quignon F, De Bels F, Koken M, Feunteun J, Ameisen J C, de The H. PML induces a novel caspase-independent death process. Nat Genet 1998; 20(3):259-65.
32. Saito S, Yamaguchi H, Higashimoto Y, et al. Phosphorylation site interdependence of human p53 post-translational modifications in response to stress. J Biol Chem 2003; 278(39):37536-44.
33. Salomoni P, Pandolfi P P. The role of PML in tumor suppression. Cell 2002; 108(2):165-70.
34. Shaulsky G, Goldfinger N, Rotter V. Alterations in tumor development in vivo mediated by expression of wild type or mutant p53 proteins. Cancer Res 1991; 51(19):5232-7.
35. Sigal A, Rotter V. Oncogenic mutations of the p53 tumor suppressor: the demons of the guardian of the genome. Cancer Res 2000; 60(24):6788-93.
36. St Clair S, Giono L, Varmeh-Ziaie S, et al. DNA damage-induced downregulation of Cdc25C is mediated by p53 via two independent mechanisms: one involves direct binding to the cdc25C promoter. Mol Cell 2004; 16(5):725-36.
37. Strano S, Dell'Orso S, Mongiovi A M, et al. Mutant p53 proteins: between loss and gain of function. Head Neck 2007; 29(5):488-96.
38. Strano S, Dell'Orso S, Di Agostino S, Fontemaggi G, Sacchi A, Blandino G. Mutant p53: an oncogenic transcription factor. Oncogene 2007; 26(15):2212-9.
39. Summerton and Weller, Antisense and Nucleic Acid Drug Development, 7:187-195, 1997.
40. Tavalai N, Papior P, Rechter S, Leis M, Stamminger T. Evidence for a role of the cellular ND 10 protein PML in mediating intrinsic immunity against human cytomegalovirus infections. J Virol 2006; 80(16):8006-18.
41. Terzian T, Suh Y A, Iwakuma T, et al. The inherent instability of mutant p53 is alleviated by Mdm2 or p16INK4a loss. Genes & Dev 2008; 22(10):1337-44.
42. Trecca D, Longo L, Biondi A, et al. Analysis of p53 gene mutations in acute myeloid leukemia. Am J Hematol 1994; 46(4):304-9.
43. Trotman L C, Alimonti A, Scaglioni P P, Koutcher J A, Cordon-Cardo C, Pandolfi P P. Identification of a tumour suppressor network opposing nuclear Akt function. Nature 2006; 441(7092):523-7.
44. Wang Z G, Delva L, Gaboli M, et al. Role of PML in cell growth and the retinoic acid pathway. Science 1998; 279 (5356):1547-51.
45. Xu Z X, Zhao R X, Ding T, et al. Promyelocytic leukemia protein 4 induces apoptosis by inhibition of survivin expression. J Biol Chem 2004; 279(3):1838-44.
46. Zimber A, Nguyen Q D, Gespach C. Nuclear bodies and compartments: functional roles and cellular signalling in health and disease. Cell Signal 2004; 16(10):1085-104.

The invention claimed is:

1. A method for treating a cancer characterized by expression of a mutant form of p53 in a subject, the method comprising administering to the subject a therapeutically effective amount of an shRNA or siRNA which inhibits promyelocytic leukemia (PML) protein, wherein said cancer is selected from the group consisting of colon adenocarcinoma, breast cancer and lung cancer and said mutant form of p53 comprises a mutation selected from the group consisting of R175H, R273H and P309S.

2. A method for inhibiting the survival and/or proliferation of tumor cells expressing a mutant form of p53, the method comprising exposing the tumor cells to an effective amount of an shRNA or siRNA which inhibits promyelocytic leukemia (PML) protein, wherein said tumor cells are selected from the group consisting of colon adenocarcinoma cells, breast cancer cells and lung cancer cells and said mutant form of p53 comprises a mutation selected from the group consisting of R175H, R273H and P309S.

3. The method of claim 1 wherein an siRNA targeted against PML mRNA is administered.

4. The method of claim 3, wherein the siRNA is targeted against SEQ ID NO: 3.

* * * * *

SEQUENCE LISTING

```
<160> NUMBER OF SEQ ID NOS: 10

<210> SEQ ID NO 1
<211> LENGTH: 19
<212> TYPE: DNA
<213> ORGANISM: Artificial Sequence
<220> FEATURE:
<223> OTHER INFORMATION: Related to PML protein-encoding sequence

<400> SEQUENCE: 1
gaccaacaac atcttctgc                                                      19
```

```
<210> SEQ ID NO 2
<211> LENGTH: 19
<212> TYPE: DNA
<213> ORGANISM: Artificial Sequence
<220> FEATURE:
<223> OTHER INFORMATION: Related to PML protein-encoding sequence

<400> SEQUENCE: 2
agatgcagct gtatccaag                                              19

<210> SEQ ID NO 3
<211> LENGTH: 19
<212> TYPE: DNA
<213> ORGANISM: Artificial Sequence
<220> FEATURE:
<223> OTHER INFORMATION: Related to PML protein-encoding sequence

<400> SEQUENCE: 3
gagtcggccg acttctggt                                              19

<210> SEQ ID NO 4
<211> LENGTH: 19
<212> TYPE: DNA
<213> ORGANISM: Artificial Sequence
<220> FEATURE:
<223> OTHER INFORMATION: Related to PML protein-encoding sequence

<400> SEQUENCE: 4
gaccaacaat atattctgc                                              19

<210> SEQ ID NO 5
<211> LENGTH: 19
<212> TYPE: DNA
<213> ORGANISM: Artificial Sequence
<220> FEATURE:
<223> OTHER INFORMATION: Related to PML protein-encoding sequence

<400> SEQUENCE: 5
agatgcagct gtatccaag                                              19

<210> SEQ ID NO 6
<211> LENGTH: 20
<212> TYPE: DNA
<213> ORGANISM: Artificial Sequence
<220> FEATURE:
<223> OTHER INFORMATION: Related to Ribosomal S18 sequence

<400> SEQUENCE: 6
ctaccacatc caaggaaggc                                             20

<210> SEQ ID NO 7
<211> LENGTH: 20
<212> TYPE: DNA
<213> ORGANISM: Artificial Sequence
<220> FEATURE:
<223> OTHER INFORMATION: Related to Ribosomal S18 sequence

<400> SEQUENCE: 7
ggcgatctcc actttaagaa                                             20

<210> SEQ ID NO 8
<211> LENGTH: 19
<212> TYPE: DNA
<213> ORGANISM: Artificial Sequence
<220> FEATURE:
<223> OTHER INFORMATION: Related to Ribosomal S18 sequence
```

```
<400> SEQUENCE: 8
cgccctggat aacgtcttt                                                19

<210> SEQ ID NO 9
<211> LENGTH: 19
<212> TYPE: DNA
<213> ORGANISM: Artificial Sequence
<220> FEATURE:
<223> OTHER INFORMATION: Related to ribosomal 18S sequence

<400> SEQUENCE: 9
ggaactgtcg tcggtgtca                                                19

<210> SEQ ID NO 10
<211> LENGTH: 18
<212> TYPE: DNA
<213> ORGANISM: Artificial Sequence
<220> FEATURE:
<223> OTHER INFORMATION: Related to p53 encoding sequence

<400> SEQUENCE: 10
gactccagtg gtaatcta                                                 18
```